(12) United States Patent
Chiragkumar

(10) Patent No.: US 9,987,226 B2
(45) Date of Patent: Jun. 5, 2018

(54) METHODS FOR FORMING MINIEMULSIONS AND USE THEREOF FOR DELIVERING BIOACTIVE AGENTS

(75) Inventor: Desai Chiragkumar, Como (AU)

(73) Assignee: NS TECHNOLOGIES PTY LTD, Mt. Lawley (AU)

( * ) Notice: Subject to any disclaimer, the term of this patent is extended or adjusted under 35 U.S.C. 154(b) by 0 days. days.

(21) Appl. No.: 13/992,435

(22) PCT Filed: Dec. 9, 2011

(86) PCT No.: PCT/AU2011/001589
§ 371 (c)(1),
(2), (4) Date: Jul. 15, 2013

(87) PCT Pub. No.: WO2012/075534
PCT Pub. Date: Jun. 14, 2012

(65) Prior Publication Data
US 2014/0322330 A1    Oct. 30, 2014

(30) Foreign Application Priority Data
Dec. 10, 2010  (AU) ............................... 2010905441

(51) Int. Cl.
*A61K 9/107* (2006.01)
*A61K 9/00* (2006.01)
*A61K 31/167* (2006.01)

(52) U.S. Cl.
CPC .......... *A61K 9/1075* (2013.01); *A61K 9/0014* (2013.01); *A61K 31/167* (2013.01)

(58) Field of Classification Search
None
See application file for complete search history.

(56) References Cited

U.S. PATENT DOCUMENTS

| | | | | |
|---|---|---|---|---|
| 3,113,029 | A * | 12/1963 | Hernandez | ...................... 426/16 |
| 5,154,930 | A * | 10/1992 | Popescu et al. | ............. 424/1.21 |
| 5,453,445 | A * | 9/1995 | Henry | ............................ 514/626 |
| 5,698,219 | A | 12/1997 | Valdivia et al. | |
| 5,952,383 | A * | 9/1999 | Metziger et al. | ............. 514/569 |
| 6,113,921 | A | 9/2000 | Friedman et al. | |
| 6,342,094 | B1 * | 1/2002 | Kabalnov | .............. C09D 11/30 106/31.25 |
| 6,551,619 | B1 * | 4/2003 | Penkler | ................. A61K 9/1075 424/400 |
| 6,743,436 | B1 * | 6/2004 | Lee et al. | ....................... 424/423 |
| 7,960,416 | B2 * | 6/2011 | Sato | ..................... A61K 9/0019 514/359 |
| 2001/0004671 | A1 * | 6/2001 | Lee | ..................... B01J 23/8885 562/531 |
| 2002/0028184 | A1 * | 3/2002 | Sunkel | ..................... A61K 8/31 424/59 |
| 2002/0065328 | A1 * | 5/2002 | Dederen | ................ A61K 8/062 516/9 |
| 2004/0182711 | A1 * | 9/2004 | Liang | ....................... B01J 13/16 204/606 |
| 2004/0198813 | A1 * | 10/2004 | Dennis | ................. A61K 9/1075 514/499 |
| 2004/0253276 | A1 * | 12/2004 | Sato et al. | ..................... 424/400 |
| 2005/0226842 | A1 | 10/2005 | Douin et al. | |
| 2006/0062810 | A1 * | 3/2006 | Woo | ...................... A61K 9/1075 424/400 |
| 2006/0127344 | A1 * | 6/2006 | Zofchak | ................... A61K 8/06 424/70.31 |
| 2007/0087104 | A1 * | 4/2007 | Chanamai | ..................... 426/602 |
| 2007/0172405 | A1 * | 7/2007 | Liu | ............................ C01F 7/02 423/121 |
| 2007/0243132 | A1 * | 10/2007 | Russell-Jones | ...... A61K 9/0014 424/1.11 |
| 2008/0044543 | A1 * | 2/2008 | McClements | ........ A23D 7/0053 426/573 |
| 2008/0199589 | A1 * | 8/2008 | Patist | ........................ A23L 2/52 426/602 |
| 2008/0234429 | A1 * | 9/2008 | Hahn | ........................ C08F 2/32 524/700 |
| 2008/0287288 | A1 * | 11/2008 | Ying et al. | ..................... 502/159 |
| 2009/0181076 | A1 * | 7/2009 | Prestidge et al. | ............. 424/450 |
| 2009/0232743 | A1 | 9/2009 | Varanasi et al. | |
| 2009/0324727 | A1 * | 12/2009 | Foguet Roca | ................ 424/489 |

(Continued)

FOREIGN PATENT DOCUMENTS

| | | | | |
|---|---|---|---|---|
| CN | 1872072 A | | 12/2006 | |
| CN | 101524330 A | * | 9/2009 | |
| EP | 211258 A2 | * | 2/1987 | ............... A61K 9/10 |

(Continued)

OTHER PUBLICATIONS

Palacios et al. Journal of the American Oil Chemists Society 2005 82:565-569.*
BASF Pluronic F127 reference (2004.*
Making Emulsions for Cosmetics www.makingcosmetics.com/articles/02-making-emulsions-for-cosmetics.pdf—2008.*
Koga et al. European Journal of Pharmaceutics and Biopharmaceutics 2000 49:17-25.*
Aafaqi Flow behavior of water-in-oil emulsions stabilized by wax crystals 2009.*
Fanun et al. Journal of Surfactants and Detergents 2010 13:321-328.*
Brime et al. Journal of Pharmaceutical Sciences 2002 91:1178-1185.*

(Continued)

*Primary Examiner* — Robert A Wax
*Assistant Examiner* — Caralynne E Helm
(74) *Attorney, Agent, or Firm* — Kilpatrick Townsend & Stockton LLP

(57) ABSTRACT

The present invention relates to methods of forming miniemulsions and use of the miniemulsions as a delivery system for bioactive agents. In particular, the present invention relates to methods for forming a miniemulsion comprising providing a first phase comprising a hydrophilic surfactant, lipophillic surfactant and water and a second phase comprising a lipid, wherein said miniemulsion comprises emulsified particles having a mean diameter of 1 µm or less.

12 Claims, 13 Drawing Sheets

(56) References Cited

U.S. PATENT DOCUMENTS

2010/0034880 A1* 2/2010 Sintov ............... A61K 9/0014
424/484

FOREIGN PATENT DOCUMENTS

| | | |
|---|---|---|
| EP | 1938801 | 7/2008 |
| JP | 63072335 A | 4/1988 |
| JP | 08099867 A | 4/1996 |
| JP | 2006008700 A | 1/2006 |
| JP | 2006273821 A | 10/2006 |
| JP | 2006342140 A | 12/2006 |
| JP | 2008536919 A | 9/2008 |
| JP | 2009505809 A | 2/2009 |
| WO | WO 9105548 A1 * 5/1991 | ........... A61K 9/0024 |
| WO | 2006115690 A2 | 11/2006 |
| WO | 2007003565 A1 | 1/2007 |
| WO | 2010018223 A1 | 2/2010 |
| WO | WO 2010018596 A2 * 2/2010 | ............... A61K 9/00 |
| WO | WO 2010141588 A1 * 12/2010 | |

OTHER PUBLICATIONS

Suzuki et al. Journal of Applied Physiology 1999 87(3):962-968.*
Brime et al. Journal of Antimicrobial Chemotherapy 2003 52:103-409.*
Borngen et al. Colloid and Polymer Science 1985 263:686-689.*
Leyck et al. Polyene phosphatidylcholine: an inhibitor of NSAID gastric toxicity which increases impaired mucosal PGE2 synthesis. Rainsford et al. ed. Side-Effects of Anti-inflammatory Drugs 1987 Lancaster:MTP Press, p. 163.*
Rakshit et al. Physicochemistry of W/O Microemulsions: Formation, Stability, and Droplet Clustering. Fanun ed. Microemulsions 2009 Boca Raton: CRC Press:Boca Raton p. 17-19.*
Jurgens et al. Pharmazie 2005 60:665-670 (Year: 2005).*
International Patent Application No. PCT/AU2011/001589, International Search Report dated Jan. 24, 2012 (2 pages).
International Patent Application No. PCT/AU2011/001589, International Preliminary Report on Patentability dated Nov. 20, 2012 (4 pages).
European Application No. 11846152.4 , EP Search Report dated Jun. 6, 2014.
Bouchemal et al., "Nano-emulsion formation using spontaneous emulsification: solvent, oil and surfactant optimisation", International Journal of Pharmaceuticals, vol. 280, No. 1-2, pp. 241-251, Aug. 2004.
Muller et al., "Solid lipid nanoparticles (SLN) for controlled drug delivery—a review of the state of the art", European Journal of Pharmaceuticals and Biopharmaceuticals, vol. 50, No. 1, pp. 161-177, Jul. 2000.
Anton et al., "Design and production of nanoparticles formulated from nano-emulsion templates—a review", Journal of Controlled Release 128.3 (2008): 185-199.
Anton et al., "The universality of low-energy nano-emulsification", International Journal of Pharmaceutics 377.1 (2009): 142-147.
Brooks et al. "Phase inversion in non-ionic surfactant—oil—water systems—II. Drop size studies in catastrophic inversion with turbulent mixing", Chemical engineering science 49.7 (1994): 1065-1075.
Friberg , "Microemulsions", Journal of Dispersion Science and Technology, 6:3, 317-337, (1985).
Griffin , "Classification of surface-active agents by" HLB"", J Soc Cosmetic Chemists 1 (1946): 311-326.
Lachman et al., The Theory and practice of industrial pharmacy 3rd ed. Philadelphia: Lea & Febiger; 1986. p. 502-533.
Martin , Physical Pharmacy: Physical Chemical Principles in the Pharmaceutical Sciences (4th ed.), Lippincott Williams & Wilkins, Philadelphia (1993).
Mason et al., "Nanoemulsions: formation structure, and physical properties", Jornal of Physics:Condens. Matter, vol. 18, 2006, pp. R635-R666.
Sajjadi , "Nanoemulsion formation by phase inversion emulsification: on the nature of inversion", Langmuir 22.13 (2006): 5597-5603.
Slomkowski et al., "Terminology of polymers and polymerization processes in dispersed systems (IUPAC Recommendations 2011)", Pure and Applied Chemistry 83.12 (2011): 2229-2259.
"The HLB System: A Time-saving Guide to Emulsifier Selection", ICI Americas, Incorporated, 1984.
Davies , "A quantitative kinetic theory of emulsion type, I. Physical chemistry of the emulsifying agent", Gas/Liquid and Liquid/Liquid Interface. Proceedings of the International Congress of Surface Activity. vol. 1. 1957.
Griffin, "Calculation of HLB values of non-ionic surfactants", Journal of the Society of Cosmetic Chemists; presented May 1954, pp. 249-256.
Griffin , "Classificate of Surface-Active Agents by "HLB"", Journal of the Society of Cosmetic Chemists; presented Oct. 1949, pp. 311-326.

* cited by examiner

| 150g batch | | 1kg batch | |
|---|---|---|---|
| Size (μm) | Number in % | Size (μm) | Number in % |
| 0.010-0.100 | 0.00 | 0.010-0.100 | 0.00 |
| 0.100-0.200 | 48.57 | 0.100-0.200 | 0.00 |
| 0.200-0.300 | 35.68 | 0.200-0.300 | 0.00 |
| 0.300-0.400 | 8.27 | 0.300-0.400 | 4.68 |
| 0.400-0.500 | 3.05 | 0.400-0.500 | 22.05 |
| 0.500-0.600 | 1.53 | 0.500-0.600 | 20.10 |
| 0.600-0.700 | 0.90 | 0.600-0.700 | 14.75 |
| 0.700-0.800 | 0.58 | 0.700-0.800 | 10.40 |
| 0.800-0.900 | 0.39 | 0.800-0.900 | 7.29 |
| 0.900-1.000 | 0.27 | 0.900-1.000 | 5.18 |
| 1.000-2.000 | 0.71 | 1.000-2.000 | 13.80 |
| 2.000-3.000 | 0.05 | 2.000-3.000 | 1.26 |
| 3.000-4.000 | 0.01 | 3.000-4.000 | 0.29 |
| 4.000-5.000 | 0.00 | 4.000-5.000 | 0.11 |
| 5.000-6.000 | 0.00 | 5.000-6.000 | 0.05 |
| 6.000-7.000 | 0.00 | 6.000-7.000 | 0.02 |
| 7.000-8.000 | 0.00 | 7.000-8.000 | 0.01 |
| 8.000-9.000 | 0.00 | 8.000-9.000 | 0.01 |

FIGURE 5

| Size (μm) | Number in % |
|---|---|
| 0.010-0.100 | 0.00 |
| 0.100-0.200 | 0.00 |
| 0.200-0.300 | 0.00 |
| 0.300-0.400 | 3.02 |
| 0.400-0.500 | 18.61 |
| 0.500-0.600 | 19.53 |
| 0.600-0.700 | 15.39 |
| 0.700-0.800 | 11.32 |
| 0.800-0.900 | 8.17 |
| 0.900-1.000 | 5.91 |
| 1.000-2.000 | 16.06 |
| 2.000-3.000 | 1.44 |
| 3.000-4.000 | 0.33 |
| 4.000-5.000 | 0.13 |
| 5.000-6.000 | 0.00 |
| 6.000-7.000 | 0.00 |
| 7.000-8.000 | 0.00 |
| 8.000-9.000 | 0.00 |

FIGURE 8(A)

| Size (µm) | Number in % |
|---|---|
| 0.010-0.100 | 0.00 |
| 0.100-0.200 | 0.00 |
| 0.200-0.300 | 0.00 |
| 0.300-0.400 | 0.22 |
| 0.400-0.500 | 12.19 |
| 0.500-0.600 | 18.02 |
| 0.600-0.700 | 16.18 |
| 0.700-0.800 | 12.80 |
| 0.800-0.900 | 9.79 |
| 0.900-1.000 | 7.39 |
| 1.000-2.000 | 21.68 |
| 2.000-3.000 | 1.58 |
| 3.000-4.000 | 0.14 |
| 4.000-5.000 | 0.01 |
| 5.000-6.000 | 0.00 |
| 6.000-7.000 | 0.00 |
| 7.000-8.000 | 0.00 |
| 8.000-9.000 | 0.00 |

FIGURE 9(A)

METHODS FOR FORMING MINIEMULSIONS AND USE THEREOF FOR DELIVERING BIOACTIVE AGENTS

CROSS-REFERENCE TO RELATED APPLICATIONS

The present application is a national phase of PCT/AU2011/001589, filed Dec. 9, 2011, which claims the benefit of priority to Australian Patent Application No. 2010905441, filed Dec. 10, 2010, each of which is incorporated herein by reference in its entirety.

FIELD

The present disclosure relates to methods of forming miniemulsions and use of the miniemulsions as a delivery system for bioactive agents. In particular, the present disclosure relates to methods of forming miniemulsions having emulsified particles of less than 1 µm from a first phase comprising a hydrophilic surfactant and a lipophilic surfactant and a second phase comprising a lipid.

BACKGROUND

An emulsion is a dispersed system consisting of two immiscible liquids, in which small droplets of one liquid is dispersed in a second liquid. Emulsions with a droplet size in the range of less than 1 µm are often referred to in the literature as miniemulsions, nano-emulsions, microemulsions, etc. These "miniemulsions" are formed by dispersion or high-energy emulsion methods such as high-shear stirring, high-pressure homogenisers and ultrasound generators.

Miniemulsions are of great interest as pharmaceutical and cosmetic formulations. In the pharmaceutical industry a major problem is the efficient and efficacious delivery of drugs. It is well known that many promising drugs never make it to a final product because of difficulties in delivery. The problems with drug delivery tend to be related to the physical or chemical properties of the drug, administrative matters, such as approval for use, excipients, and engineering issues. Some of the major challenges of drug delivery are poor solubility, short in vitro (shelf-life) and in vivo (half-life) stability, low bioavailability, unacceptable side effects (due to systemic delivery) and regulatory issues.

A drug delivery system or formulation should have the following characteristics: ease of production, applicability to as many drugs as possible, physical stability, excipients that are well tolerated and accepted by regulatory authorities and available for large scale production allowable by regulatory authorities. Miniemulsions have properties that make them ideal for use in drug delivery including thermodynamic stability (long shelf-life), ease of formation, high surface area (high solubilisation capacity) and very small droplet size.

However, there are problems associated with the available miniemulsion formulations. High levels of non-active compounds are a hazard in cosmetics and drug delivery systems and many miniemulsions have high surfactant concentrations and in most cases have a high alcohol, solvent and co-solvent content in order to maintain stability. Further, many miniemulsions are created using high-energy processes, such as high pressures and high temperatures. For example, high temperatures are used to induce stability, which makes commercial production expensive. Additionally, miniemulsions created using processes such as ultrasonic emulsification, which are only useful for creating small batches, means reproducibility of the emulsion during commercial scale up is difficult.

Accordingly, the methods that are currently available for making miniemulsions that are feasible for formulating product are constrained. As such, there is a need for improved methods and formulations for miniemulsions for use as delivery systems for bioactive agents.

SUMMARY

The methods disclosed herein relate to miniemulsion formulations formed by low-energy methods that are suitable for large commercial production, have a low surfactant content, are stable without refrigeration for up to three years and can be used to deliver a wide-range of bioactive agents by a variety of routes. Accordingly, the methods disclosed herein provide, in some aspects, a miniemulsion that is suitable for use as a delivery system for bioactive agents.

In a first aspect, there is disclosed a method for forming a miniemulsion comprising:
  a. providing an aqueous phase comprising a hydrophillic surfactant dispersed in water;
  b. dispersing a lipophillic surfactant in said aqueous phase to provide a first phase;
  c. providing a second phase comprising a lipid;
  d. adding the second phase to the first phase in a manner adapted to form a miniemulsion, wherein said miniemulsion comprises emulsified particles having a mean diameter of less than 1 µm.

It will be understood that any manner adapted to form a miniemulsion known in the art could be used to form the miniemulsion, for example, stirring or other suitable mixing means. Preferably, the manner adapted to form a miniemulsion is a low-energy manner. Accordingly, in one embodiment, the manner adapted to form a miniemulsion comprises adding the second phase to the first phase as a continuous flow or continuous stream during continuous mixing. In another embodiment, the manner adapted to form a miniemulsion comprises adding the second phase to the first phase under controlled flow during continuous mixing. In a further embodiment, manner adapted to form a miniemulsion comprises adding the second phase drop wise into the first phase during continuous mixing. Generally, the continuous mixing is performed by a stirrer at a speed of between about 5,000 rpm and about 20,000 rpm.

Accordingly, a miniemulsion according to the present disclosure can be formed in the absence of high temperatures or pressures. In one embodiment, steps a.-d. are conducted at a temperature of less than about 80° C., preferably less than about 60° C. and more preferably steps a.-d. are conducted at a temperature of 40° C. or less. In another embodiment, steps a.-d. are conducted at an atmospheric pressure of less than about 1,000 kPa, preferably about less than about 500 kPa and more preferably steps a.-d. are conducted at normal atmospheric pressure (about 101 kPa). In still another embodiment, the method does not comprise a cooling step. In a particular embodiment, step d. is conducted at a temperature of 40° C. or less and at normal atmospheric pressure (about 101 kPa).

Therefore, in one embodiment there is disclosed a method for forming a miniemulsion comprising:
  a. providing an aqueous phase comprising a hydrophillic surfactant dispersed in water;
  b. dispersing a lipophillic surfactant in said aqueous phase to provide a first phase;
  c. providing a second phase comprising a lipid;

d. adding the second phase to the first phase in a manner adapted to form a miniemulsion, wherein step d. is conducted at a temperature of 40° C. or less and at normal atmospheric pressure (about 101 kPa), and wherein said miniemulsion comprises emulsified particles having a mean diameter of less than 1 µm.

It would be appreciated that any hydrophilic or lipophilic surfactant may be used in the formation of the first phase. While any hydrophilic surfactant know in the art could be used, in one embodiment the hydrophilic surfactant is selected from the group consisting of polyoxyethylene alkyl ethers; sorbitan fatty acid esters; polyoxyethylene alkyl phenols; polyoxyethylene glycol esters; polyoxypropylene glycol alkyl ethers; polyglycerol fatty acid esters; polyoxyethylene glycerides; polyoxyethylene sterols; polyoxyethylene vegetable oils; polyoxyethylene hydrogenated vegetable oils; propylene glycol alginate; salts of fatty acids; lauryl macrogolglycerides; and mixtures thereof.

Similarly, any lipophilic surfactant known in the art could be used. However, in one embodiment, the lipophilic surfactant is selected from the group consisting of fatty acids; acetylated glycerol fatty acid esters; lower alcohol fatty acids esters; trans-esterification products of fatty acids; hydrogenated vegetable oils; triglycerides and polyalkylene polyols; sterols and sterol derivatives; pentaerythritol fatty acid esters and polyalkylene glycol ethers; monoglycerides and acetylated; lecithins and hydrogenated lecithins; lysolecithin and hydrogenated lysolecithins; lysophospholipids and derivatives thereof; phospholipids and derivatives thereof; and mixtures thereof. In one aspect, the hydrophilic surfactant is a non-ionic surfactant such as polysorbate 80 and the lipophilic surfactant is a phosphotidylcholine.

In some embodiments, the method relates to a miniemulsion that has a low surfactant content. In one embodiment, the miniemulsion comprises less than 10% w/w surfactant. In another embodiment, the miniemulsion comprises between about 1% w/w and about 5% w/w lipophilic surfactant and between about 0.5% w/w and about 5% w/w hydrophilic surfactant. In one embodiment, the method may further comprise the addition of a solvent to either the first or second phase.

In some embodiments, the method relates to a miniemulsion that has a high oil content. In one embodiment, the miniemulsion comprises at least about 0.5% w/w, or for example, from about 0.5% w/w to about 40% w/w, from about 0.5% w/w to about 15% w/w, or from about 15% w/w to about 25% w/w oil, or from about 25% w/w to about 40% w/w oil.

The lipid may be any lipid known in the art including vegetable derived lipids, animal derived lipids, and mineral oils. Preferably the lipid is a vegetable oil comprising medium or long-chain fatty acids with aliphatic tails of 6 carbons or longer. Examples of vegetable oils suitable for use in the present method include coconut oil, castor oil, arachis oil, corn oil, cottonseed oil, olive oil, palm oil, rapeseed oil, including Canola oil, safflower oil, soybean oil, liquid paraffin and sunflower oil and their derivatives. In one embodiment, the oil is soybean oil. In another embodiment, the lipid is an animal derived lipid such as phosphatidylcholine.

The emulsified particles can have a wide variety of shapes and structures having sizes, in general, that are 1 µm or less. In one aspect, emulsified particles have a mean particle size of less than 1 µm. In one embodiment, the mean particle size is between about 250 nm and 1 µm. In another embodiment, the range of mean particle size is from about 300 nm to about 700 nm. In yet another embodiment, the mean particle size is about 600 nm. In a further embodiment, at least 70% of the particles in the miniemulsion have a diameter of 1 µm or less. In a still further embodiment, at least 75% of the particles in the miniemulsion have a diameter of less than 1 µm.

Accordingly, in one aspect, there is disclosed a method for forming a miniemulsion comprising:
 a. providing an aqueous phase comprising a hydrophillic surfactant dispersed in water;
 b. dispersing a lipophillic surfactant in said aqueous phase to provide a first phase;
 c. providing a second phase comprising a lipid;
 d. adding the second phase to the first phase in a manner adapted to form a miniemulsion,
wherein the range of mean particle sizes is from about 250 nm to about 700 nm.

In another aspect, there is disclosed a method for forming a miniemulsion comprising:
 a. providing an aqueous phase comprising a hydrophillic surfactant dispersed in water;
 b. dispersing a lipophillic surfactant in said aqueous phase to provide a first phase;
 c. providing a second phase comprising a lipid;
 d. adding the second phase to the first phase in a manner adapted to form a miniemulsion,
wherein at least 70% of the particles in the miniemulsion have a diameter of 1 µm or less.

The method disclosed herein provides a miniemulsion that is stable without refrigeration for up to three years. Therefore, the miniemulsion does not coalesce and maintains particle size when stored at a temperature greater than 4° C. In one embodiment, the miniemulsion is stable at a temperature greater than 4° C. for at least 1 month, preferably at least 6 months and more preferably the miniemulsion is stable at a temperature greater than 4° C. for at least 1 year. In another embodiment, the miniemulsion is stable at a temperature greater than 4° C. for at least two years. In another embodiment, the miniemulsion is stable at a temperature greater than 4° C. for more than two years.

In a second aspect, there is disclosed a method for forming a miniemulsion consisting essentially of:
 a. providing an aqueous phase comprising a hydrophillic surfactant dispersed in water;
 b. dispersing a lipophillic surfactant in said aqueous phase to provide a first phase;
 c. providing a second phase comprising a lipid;
 d. adding the second phase to the first phase in a manner adapted to form a miniemulsion,
wherein said miniemulsion comprises emulsified particles having a mean diameter of less than 1 µm.

In one embodiment, the steps of the method are carried out in a particular order such that multilayered and/or spherical emulsified particles are formed. In accordance with this embodiment steps (a), (b) and (c) are performed before step (d). Therefore, a first phase is formed comprising a hydrophilic surfactant, water and lipophilic surfactant and a second phase is formed comprising lipid, before the first and second phases are combined in step (d).

Accordingly, in one embodiment there is disclosed a method for forming a miniemulsion comprising:
 a. providing an aqueous phase comprising a hydrophillic surfactant dispersed in water;
 b. dispersing a lipophillic surfactant in said aqueous phase to provide a first phase;
 c. providing a second phase comprising a lipid;
 d. adding the second phase to the first phase in a manner adapted to form a miniemulsion, wherein steps (a), (b) and (c) are performed before step (d), and wherein said miniemulsion comprises emulsified particles having a mean diameter of less than 1 µm.

In another embodiment, there is disclosed a method for forming a miniemulsion comprising:
a. providing an aqueous phase comprising a hydrophillic surfactant dispersed in water;
b. dispersing a lipophillic surfactant in said aqueous phase to provide a first phase;
c. providing a second phase comprising a lipid;
d. adding the second phase to the first phase in a manner adapted to form a miniemulsion,
wherein said miniemulsion comprises emulsified particles having a mean diameter of less than 1 µm, and wherein said emulsified particles are multilayered and/or spherical.

In some aspects, the miniemulsion described herein may be used as a delivery system for one or more bioactive agents. While a person skilled in the art would understand that a bioactive agent could be incorporated into the miniemulsion via the first, second or both phases, in one embodiment, the second phase further comprises a bioactive agent. In another embodiment, the miniemulsion comprises between about 0.2% w/w and 15% w/w bioactive agent.

Accordingly, in a third aspect, there is disclosed a method for forming a delivery system for bioactive agents comprising;
a. providing an aqueous phase comprising a hydrophilic surfactant dispersed in water;
b. dispersing a lipophilic surfactant in said aqueous phase to provide a first phase;
c. providing a second phase comprising a lipid and a bioactive agent;
d. adding the second phase to the first phase in a manner adapted to form a miniemulsion,
wherein said delivery system comprises emulsified particles having a mean diameter of less then 1 µm.

In one embodiment, there is disclosed a method for forming a delivery system for bioactive agents comprising;
a. providing an aqueous phase comprising a hydrophilic surfactant dispersed in water and a bioactive agent;
b. dispersing a lipophilic surfactant in said aqueous phase to provide a first phase;
c. providing a second phase comprising a lipid;
d. adding the second phase to the first phase in a manner adapted to form a miniemulsion,
wherein said delivery system comprises emulsified particles having a mean diameter of less then 1 µm.

It will be understood that the presently described delivery system may be used to deliver any bioactive agent. In one embodiment, the bioactive agent is a lipophilic pharmaceutical. In another embodiment, the bioactive agent is lidocaine or lignocaine.

As a result of having particles of 1 µm or less, the delivery system may be used to administer bioactive agents by a variety of routes, for example, topically, enterally, nasally or parenterally. In one embodiment, topical administration is via aerosol or spray.

In a fourth aspect, there is disclosed a method for forming a delivery system for bioactive agents comprising;
a. providing an aqueous phase comprising polysorbate 80 dispersed in water;
b. dispersing phosphotidylcholine in said aqueous phase to provide a first phase;
c. providing a second phase comprising soybean oil and lidocaine;
d. adding the second phase to the first phase in a manner adapted to form a miniemulsion comprising between about 0.5% w/w and about 5% w/w polysorbate 80, between about 1% w/w and about 5% w/w phosphotidylcholine, between about 0.5% w/w and about 25% w/w soybean oil, and between about 0.2% w/w and about 5% w/w lidocaine,
wherein said delivery system comprises emulsified particles having a mean diameter of less then 1 µm.

In fifth aspect, there is disclosed a method for forming a delivery system for bioactive agents consisting of;
a. providing an aqueous phase comprising polysorbate 80 dispersed in water;
b. dispersing phosphotidylcholine in said aqueous phase to provide a first phase;
c. providing a second phase comprising soybean oil and lidocaine;
d. adding the second phase to the first phase in a manner adapted to form a miniemulsion comprising between about 0.5% w/w and about 5% w/w polysorbate 80, between about 1% w/w and about 5% w/w phosphotidylcholine, between about 0.5% w/w and about 25% w/w soybean oil, and between about 0.2% w/w and about 5% w/w lidocaine,
wherein said delivery system comprises emulsified particles having a mean diameter of less then 1 µm.

It will be understood that in one aspect there is disclosed compositions comprising emulsified particles produced by the above described methods.

In a further aspect, the delivery system described above is formulated into a composition useful in the treatment or relief of pain in a subject in need thereof.

BRIEF DESCRIPTION OF THE FIGURES

FIG. 5: Particle size distribution for miniemulsions prepared in batch sizes of 150 g and 1 kg.

DETAILED DESCRIPTION OF THE PREFERRED EMBODIMENTS

Figure 1:
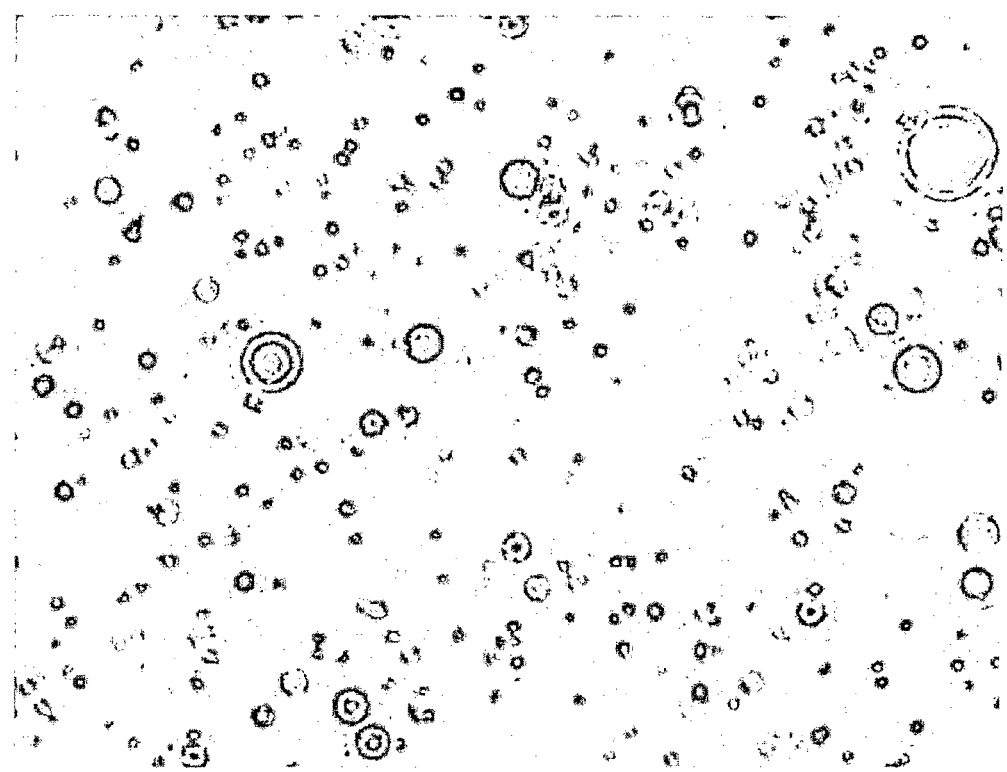
FIG. 1: Photograph of a miniemulsion by fluorescence microscope (400×).

It is to be understood that this disclosure is not limited to particularly exemplified methods and may, of course, vary. It is also to be understood that the terminology used herein is for the purpose of describing particular embodiments only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the disclosed methods. Nothing herein is to be construed as an admission that what is disclosed herein is not entitled to antedate such disclosure by virtue of prior invention.

In this specification and in the claims that follow, reference will be made to a number of terms that shall be defined to have the following meanings:

The term "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It must be noted that, as used in the specification and the appended claims, the singular forms "a," "an" and the include plural referents unless the context clearly dictates otherwise. Thus, for example, reference to "a bioactive agent" includes mixtures of two or more such agents, and the like.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance can or cannot occur, and that the description includes instances where the event or circumstance occurs and instances where it does not.

A weight percent of a component, unless specifically stated to the contrary, is based on the total weight of the formulation or composition in which the component is included.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

A "low-energy manner" refers to a process that does not involve heating to a high tempertaure, cooling or the use of high pressures. Examples of low-energy manner adapted to form a miniemulsion useful in the present method include those that are performed at room temperature, ie. about 25° C., those that do not require a significant heating step, ie. heating greater than about 40° C., and/or a cooling step and those that are performed at about normal atmospheric pressure at sea level, ie. about 101.325 kPa.

The term "refrigeration" refers to storing a microemulsion at a temperature that is lower than room temperature, ie. less than about 25° C. More specifically, refrigeration may relate to storing a microemulsion at 10° C. or less, and in particular 4° C. or less. Accordingly, the term "without refrigeration" relates to a temperature at least greater than 4° C.

In the broadest aspect, there is disclosed a method for forming a miniemulsion. The method involves preparing an aqueous phase by combining water and one or more hydrophilic surfactants. In one embodiment the surfactant component comprises a hydrophilic surfactant. In another embodiment, the surfactant component consists of a single hydrophilic surfactant, and in another embodiment, the hydrophilic surfactant component comprises more than one hydrophilic surfactant. The hydrophilic surfactant may be selected from but not limited to the group comprising of polyoxyethylene alkyl ethers; sorbitan fatty acid esters known as Polysorbates; polyoxyethylene alkyl phenols; polyoxyethylene glycol esters; polyoxypropylene glycol alkyl ethers; polyglycerol fatty acid esters; polyoxyethylene glycerides; polyoxyethylene sterols; polyoxyethylene vegetable oils; polyoxyethylene hydrogenated vegetable oils; propylene glycol alginate; salts of fatty acids; laiiryl macrogolglycerides, or mixtures thereof. Preferably, the hydrophilic surfactant is a non-ionic surfactant. Non-limiting examples of suitable hydrophilic non-ionic surfactants that may be suitable for use in the present method include sorbitan fatty acid esters (Polysorbates), polyoxyethylene glycol, polyoxyethylene glycol alkyl ethers, and polyoxypropylene glycol alkyl ethers. In one embodiment, the non-ionic surfactant used is polysorbate 80 (Tween 80®).

After combining the hydrophilic surfactant and the water, the solution is processed until the hydrophilic surfactant disperses. The hydrophilic surfactant may be dispersed by any mixing means know in the art. Examples of suitable mixing means are described infra. In one embodiment, the hydrophilic surfactant is dispersed by stirring. In another embodiment, the hydrophilic surfactant is dispersed by stirring at a speed of between about 5,000 rpm and about 10,000 rpm. Once dispersed this solution forms the aqueous phase.

A "first phase" is formed by dispersing a lipophilic surfactant in the aqueous phase. The lipophilic surfactant may be selected from but not limited to the group comprising of fatty acids; sorbitan fatty acid esters; acetylated glycerol fatty acid esters; lower alcohol fatty acids esters; trans-esterification products of fatty acids, glycerides, vegetable oils, hydrogenated vegetable oils, triglycerides and polyalkylene polyols; sterols and sterol derivatives; pentaerythritol fatty acid esters and polyalkylene glycol ethers; monoglycerides and acetylated, e.g. mono- and di-acetylated monoglycerides; lecithins and hydrogenated lecithins; lysolecithin and hydrogenated lysolecithins; lysophospholipids and derivatives thereof; phospholipids and derivatives thereof; or mixtures thereof. Preferably, the lipophilic surfactant is a phospholipid. Phospholipids are amphiphilic molecules and may act as surfactants. Phospholipids suitable for use include phosphatidic acid (phosphatidate), phosphatidylethanolamine (cephalin), phosphatidylcholine (lecithin), phosphatidylserine, and phosphoinositides. A mixture of various phospholipids may also be used. In one embodiment, the phospholipid is lecithin. In another embodiment, the phospholipid is phosphatidylcholine enriched lecithin (Epikuron™). The phospholipid may be dispersed by a mixer, as described infra. In one embodiment, the phospholipid is dispersed by the use of a stirrer at a speed of between about 10,000 rpm and about 20,000 rpm.

Without wishing to be bound by any particular theory or hypothesis, the inventors believe that the addition of a lipophilic surfactant to the aqueous phase creates a robust multilayered/sperical micellar structure or liposomal structure due to presence of the hydrophilic surfactant. This multilayer micellar structure is thought to increase the surface area of the interface, which facilitates access to the surfactant during the emulsification process.

Accordingly, in some aspects, the steps of the method are carried out in a particular order in order to promote the formation of multilayered/spherical micelle structures. In accordance with these aspects, step (a), (b) and (c) are carried out before step (d). Therefore, a first phase is formed comprising a hydrophilic surfactant, water and lipophilic surfactant and a second phase is formed comprising lipid, before the first and second phases are combined in step (d). Further, in one embodiment, the miniemulsion comprises multilayered/spherical emulsified particles.

Miniemulsions of the prior art generally contain high surfactant concentrations (greater than 10%) in order to maintain stability. For example, WO2010/093523 describes a microemulsion comprising a co-surfactant from about 10% to about 20% by weight and a surfactant, from about 15% to about 40% by weight. Similarly, WO2010/092596 describes a microemulsion having a range of concentration of surfactant/co-surfactant from 15 to 96% (v/v). Although the amount of surfactant in the first phase and in the resultant miniemulsion described herein will, of course, vary depending on the type of surfactants used and other factors, such as the intended use, the miniemulsion comprises generally a low concentration of surfactant. The miniemulsion can comprise 2% w/w, 4% w/w, 5% w/w, 6% w/w, 8% w/w, or 10% w/w surfactant, including any range between the disclosed percentages. In one embodiment, the miniemulsion comprises less than 10% w/w surfactant. In another embodiment, the miniemulsion comprises between about 1% w/w and about 5% w/w lipophilic surfactant and between about 0.5% w/w and about 5% w/w hydrophilic surfactant.

Critical micelle concentration (CMC) is defined as the concentration of surfactants above which micelles are spontaneously formed. Upon introduction of surfactants (or any surface active materials) into the system they will initially partition into the interface, reducing the system free energy by a) by lowering the energy of the interface and b) by removing the hydrophobic parts of the surfactant from contacts with water.

Subsequently, when the surface coverage by the surfactants increases and the surface free energy (surface tension) decreases and the surfactants start aggregating into micelles, thus again decreasing the system's free energy by decreasing the contact area of hydrophobic parts of the surfactant with water. Upon reaching CMC, any further addition of surfactants will just increase the number of micelles (in the ideal case).

These micellar or liposomal structures make the lipophilic surfactant readily available at interface to the lipid when the second phase is added, promoting formation of emulsified particles. Provided below is a table of commonly used non-ionic surfactants and their CMC value:

| No. | Surfactant Trade name | CMC (mM) |
|---|---|---|
| 1 | Tween 20 | 0.05 |
| 2 | Tween 40 | 0.023 |
| 3 | Tween 60 | 0.021 |
| 4 | Tween 80 | 0.01 |
| 5 | Tween 65 | 0.00018 |
| 6 | Tween 85 | 0.00029 |
| 7 | Myrj 45 | 0.373 |
| Triton X (TX) series | | |
| 8 | TX-15 | 0.0145 |
| 9 | TX-35 | 0.047 |
| 10 | TX-45 | 0.1 |
| 11 | TX-114 | 0.168 |
| 12 | TX-100 | 0.24 |
| 13 | TX-102 | 0.35 |
| 14 | TX-165 | 0.439 |
| 15 | TX-305 | 0.72 |
| 16 | TX-405 | 0.81 |
| 17 | TX-705 | 1.0413 |
| Brij Series | | |
| 18 | Brij 30 | 0.004 |
| 19 | Brij 35 | 0.06 |
| 20 | Brij 52 | 0.000067 |
| 21 | Brij 56 | 0.002 |
| 22 | Brij 58 | 0.007 |
| 23 | Brij 72 | 0.00025 |
| 24 | Brij 76 | 0.003 |
| 25 | Brij 78 | 0.0057 |
| 26 | Brij 92 | 24.845 |
| 27 | Brij 97 | 0.94 |
| 28 | Brij 99 | 0.265 |
| 29 | Brij 700 | 0.02 |
| 30 | Brij 721 | 0.0039 |
| 31 | Phospholipid D7PC | 1.9 |

While not wishing to be bound by any hypothesis, generally the concentration of surfactant is higher than the CMC in the final system. However, a person skilled in the art would appreciate that a specific range cannot be delineated due to complex behaviour of surfactant in the system and because CMC values change with according to the presence of solvent and differences in temperature.

The method described herein also involves preparing a "second phase" comprising a lipid. The lipid may be any lipid known in the art including vegetable derived lipids, animal derived lipids, and mineral oils. Preferably the lipid is a vegetable oil comprising medium or long-chain fatty acids with aliphatic tails of 6 carbons or longer. Examples of vegetable oils suitable for use in the present method include coconut oil, castor oil, arachis oil, corn oil, cottonseed oil, olive oil, palm oil, rapeseed oil, including Canola oil, safflower oil, soybean oil, and sunflower oil and their derivatives. In one embodiment, the oil is soybean oil. In another embodiment, the lipid is an animal derived lipid such as phosphatidylcholine.

The miniemulsion can comprise 0.5% w/w, 2% w/w, 5% w/w, 10% w/w, 15% w/w, 20% w/w, 25% w/w, 30% w/w or 40% w/w lipid, including any range between the disclosed percentages. In one embodiment, the miniemulsion comprises at least about 0.5% w/w, or for example, from about 0.5% w/w to about 40% w/w, from about 0.5% w/w to about 15% w/w, or from about 15% w/w to about 25% w/w oil, or from about 25% w/w to about 40% w/w oil.

Optionally, dispersion of the lipid may be aided by the addition of a solvent to either the first or second phase. Suitable solvents would be well known to a person skilled in the art. Examples of suitable solvents include acetone (2-propanone, propan-2-one), 1-butanol (n-butyl alcohol), 2-butanol (butan-2-ol), ethanol (ethyl alcohol), ethyl acetate (acetic acid ethyl ester), heptane (n-heptane), 3-methyl-1-butanol (isoamyl alcohol, isopentyl alcohol), methylethylketone (2-butanone, MEK, butane-2-one), 2-methyl-1-propanol (isobutyl alcohol, 2-methylpropan-1-ol), pentane (n-pentane), 1-Pentanol (amyl alcohol, pentan-1-01), 1-propanol (propan-1-ol, propyl alcohol), 2-propanol (propan-2-ol, isopropyl alcohol, IPA). Preferably the solvent is a water miscible (hydrophilic) solvent, for example, propanol, isopropyl alcohol, ethanol, or acetone. In one embodiment, the first or second phase further comprises between about 5 g and about 20 g of propanol.

Once the first and second phases have been prepared, the second phase is added to the first phase in a manner adapted to form an oil-in-water miniemulsion. Suitable manners that are adapted to form miniemulsions would be well known to a person skilled in the art. Preferably, the manner adapted to form a miniemulsion and other processes used to form the miniemulsion described herein are low-energy. Generally, high-energy processes are required to produce particles having a mean size of 1 μm or less. For example, generally a doubling of energy dissipation (energy consumption) may cause a reduction of average particle size of about 25% when using conventional formulations.

Energy consumption may take place in various forms, for example, it can be the energy needed by the stirrer to overcome shear force resistance of the miniemulsion in a batch process, the energy for heating and cooling, and/or the power to overcome pressure drop. For example, WO2008/128779 describes forming a microemulsion by mixing an oily phase with an aqueous phase using high energy shear processes such as high pressure homogenisation or sonication. Heating is often needed for emulsification when one of the phases does not flow or flows too slowly at room temperature. WO2006/024095 describes a step of heating in the range of 40-99° C., preferably 45-95° C., more preferably 65-85° C. with continuous mixing to obtain an oil in water microemulsion. A heated emulsion typically has lower stability due to lower viscosity of the continuous phase and in turn less drag. Drag may be necessary to stop or resist the motion of the droplets and in turn the coalescence into larger and often undesired droplets or aggregates of droplets as well as phase separation into layers. After emulsification, droplets tend to rise by buoyancy. As such, an immediate cooling down step may be needed, which also consumes energy.

In contrast, the method described herein does not require significant heating (and as such does not require cooling) or pressure to form a stable miniemulsion. Therefore, the miniemulsion disclosed can be formed in the absence of high temperatures. Generally, formation of the miniemulsion described herein is conducted at a temperature of less than about 80° C., preferably less than about 60° C. and more preferably at a temperature of 40° C. or less. Further, as the method disclosed herein does not utilise high temperature, there is no cooling step required. While ancillary steps, such as the sterilisation of materials, may involve high temperatures, a person skilled in the art would appreciate that such steps in no way facilitate the formation of the miniemulsion.

The miniemulsion disclosed herein can also be formed in the absence of high pressures. Typically, the formation of the miniemulsion described herein is conducted in a chamber having a pressure of less than about 1,000 kPa, preferably about less than about 500 kPa and more preferably at normal atmospheric pressure (about 101 kPa). In one embodiment, the addition of the second phase to the first phase is conducted at a temperature of 40° C. or less and at normal atmospheric pressure (about 101 kPa).

Accordingly, the manners adapted to form a miniemulsion used in the present method are considerably lower in energy consumption than those used to form conventional miniemulsions. For example, in one aspect, the miniemulsion can be formed by stirring using a magnetic stirrer, overhead stirrer or other suitable stirring means. In another aspect, the formation of the miniemulsion can be aided by a mixer. In one aspect, for example, the second phase is added in a drop wise fashion to a continuous mixer containing the first phase. The continuous mixer can comprise any suitable mixing means, including a static and/or dynamic mixer. The mixer can be any mixer comprising mechanical or non-mechanical mixing parts.

The continuous mixer may comprise a stirrer having static mixing arms that create turbulence in the flow such that the first and second phases are mixed to thereby form the miniemulsion. In other aspects, the continuous mixer comprises an emulsifier, an emulsification device, or a homogeniser (e.g., an in-line or continuous homogeniser or a rotor/stator homogeniser). Examples include, without limitation, packed-bed emulsifiers, screen, and membrane emulsifiers. In one aspect, the continuous mixer is stirrer that has mixing parts that can mix the phases at a desired revolutions per minute (rpm), such as from about 5,000 rpm to about 20,000 rpm. In one embodiment, the second phase is added to the first phase as a continuous flow or continuous stream during continuous mixing. In another embodiment, the second phase is added to the first phase under controlled flow during continuous mixing. In a further embodiment, the continuous mixing is with a rotor homogeniser at a speed up to about 20,000 rpm.

In general, any emulsified particles can be produced by the methods disclosed herein. The emulsified particles can have a wide variety of shapes and structures, including spherical, multilayered, microcapsule, microsphere, nanoparticle, nanocapsule and nanosphere, having sizes from about 10 nm to 1 μm and as well as particles, in general, that are less than about 1 μm. The miniemulsion can comprise particles having a mean size between about 10 nm to about 900 nm, about 20 nm to about 800 nm, and about 50 nm to about 850 nm, including any range between the disclosed ranges. However, generally, miniemulsions produced by the methods disclosed herein have a mean particle size of between 250 nm and 1 μm. In one aspect, the disclosed emulsified particles have a mean particle size of less than 1 μm. In one embodiment, the range of mean particle size is from about 250 nm to about 1 μm. In yet another embodiment, the range of mean particle size is from about 300 nm to about 700 nm. In still another embodiment, the mean particle size is about 600 nm. In a further embodiment, at least 70% and most preferably at least 75% of the particles in the miniemulsion are 1 μm or less.

Particle size distributions are measured by laser diffraction techniques known to those of skill in the art. Optionally, the miniemulsion may undergo sonication and/or high pressure homogenisation and/or increase the mixing time to further reduce the particle size, if required.

The miniemulsion formed by the method described above is stable without refrigeration for extended periods of time. When an emulsion becomes unstable it separates or coalesces into its component phases and a layer of lipid or oil becomes visible. An increase in particle size also indicates that the emulsion is becoming unstable. As discussed above, methods of determining particle size are known to those skilled in the art. Therefore, the miniemulsion described herein is stable in that after an extended period of time the miniemulsion still has a mean particle size of 1 µm or less. In one embodiment, the miniemulsion described herein is stable from at least one month up to about three years without refrigeration. Preferably, the miniemulsion is stable without refrigeration for at least about one year. More preferably, the miniemulsion is stable without refrigeration for at least about two years. In one embodiment, after about three years at least 70% of the particles are 1 µm or less. In another embodiment, after about three years the mean particle size has increased by less than 0.05 µm.

In one aspect, a miniemulsion provided by a method described above may be formulated to include a bioactive agent or multiple bioactive agents in combination. A wide variety of bioactive agents can be used with the methods described herein. A liquid or solid bioactive agent can be incorporated into the miniemulsion described herein. The bioactive agents can include salts of the active ingredient. As such, the bioactive agents can be acidic, basic, or amphoteric salts. They can be non-ionic molecules, polar molecules, prodrugs, solvates, polymorphs or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents that may be incorporated into systems herein include, but are not limited to, peptides, proteins such as hormones, enzymes, antibodies, antibody fragments and the like, nucleic acids such as aptamers, siRNA, DNA, RNA, antisense nucleic acid or the like, antisense nucleic acid analogs or the like, low-molecular weight compounds, or high-molecular weight compounds. Bioactive agents contemplated for use in the disclosed miniemulsion include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, antitussive agents, anti-uricemic agents, anti-vascular growth agents, anti-vascular endothelial growth agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, vascular growth agents, vascular endothelial growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents in the miniemulsion include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anticholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, beta-adrenergic blocking agents, alpha-adrenergic antagonists, nutritional agents, opium alkaloids and the benzophenanthridine alkaloids. The agent can further be a substance capable of acting as a stimulant, sedative, hypnotic, analgesic, anticonvulsant, and the like.

Other bioactive agents include but are not limited to the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin. Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, or a combination thereof.

The bioactive agent can also be an immunomodulator, including, for example, cytokines, interleukins, interferon, colony stimulating factor, tumour necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens, Neisseria meningitides, Neis-* seria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, *rubella*, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia rickettsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, analgesics such as acetaminophen, acetylsalicylic acid, and the like; anesthetics such as lidocaine, lignocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antimicrobials such as cetrimide, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, papaverine, and the like; vitamins and minerals such as essential amino acids, calcium, iron, potassium, zinc, vitamin B 12, vitamin C, vitamin D and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxam®, Herceptin, alpha-glucosidase, Cerazyme/Ceredose®, vasopressin, ACTH, human serum albumin, gamma globulin, structural proteins, blood product proteins, complex proteins, enzymes, antibodies, monoclonal antibodies, antibody fragments, and the like; prostaglandins such as prostaglandin E1, prostaglandin 12, prostaglandin E2, and the like; nucleic acids; carbohydrates; fats; narcotics such as morphine, codeine, and the like; psychotherapeutics; nonsteroidal anti-inflammatory agents such as ibuprofen, diclofenac and the like; antihypertensive agents such as phentolamine HCl, and the like; anti-malarials, L-dopa, diuretics such as furosemide, spironolactone, and the like; antiulcer drugs such as ranitidine HCl, cimetidine HCl, and the like.

In certain aspects, the bioactive agent can be present as a component in a pharmaceutical composition. Pharmaceutical compositions can be conveniently prepared in a desired dosage form, including, for example, a unit dosage form or controlled release dosage form, and prepared by any of the methods well known in the art of pharmacy. In general, pharmaceutical compositions are prepared by uniformly and intimately bringing the bioactive agent into association with a liquid carrier or a finely divided solid carrier, or both. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other pharmaceutically acceptable carriers or components that can be mixed with the bioactive agent can include, for example, a fatty acid, a sugar, a salt, a water-soluble polymer such as polyethylene glycol, a protein, polysacharride, or carboxmethyl cellulose, a surfactant, a plasticizer, a high- or low-molecular weight porosigen such as polymer or a salt or sugar, or a hydrophobic low-molecular weight compound such as cholesterol or a wax.

The method of incorporating the bioactive agent into the miniemulsion will be dependent on the properties of the bioactive agent. For example, a lipophillic agent will generally be dissolved in the lipid and be dispersed with the lipid in the lipid droplet, while a hydrophilic agent will generally be dissolved in the aqueous phase. However, hydrophilic and lipophilic agents may also be chemically or physically bound to polymers, lipids and/or surfactants. Methods of incorporating the bioactive agent into the miniemulsion would be well known to persons skilled in the art (see, for example, Hendrickson, R. Ed. Remington: The Science and Practice of Pharmacy, 21st ed.; Lippincott Williams & Wilkins: Baltimore Md., 2005).

In one embodiment, the second phase comprises lipid and a bioactive agent. It will be apparent that the presently disclosed methods provide, in one aspect, a high concentration of bioactive active agent, relative to the size of the emulsified particle. As described supra, the miniemulsion described here can contain up to 40% w/w oil. This high oil content allows a high concentration of bioactive agent to be incorporated into the miniemulsion. For example, the miniemulsion can comprise 0.1% w/w, 0.5% w/w, 2% w/w, 3% w/w, 5% w/w, 10% w/w, 15% w/w, 30% w/w or 40% w/w bioactive agent, including any range between the disclosed percentages. In one embodiment, the miniemulsion comprises at least about 0.2% w/w, or for example, from about 0.2% w/w to about 8% w/w, or from about 10% w/w to about 15% w/w bioactive agent.

In a particular aspect, the preferred bioactive agent is a "hydrophobic compound" or "lipophilic compound". The term "hydrophobic compound" refers to a compound with limited water solubility. The term "lipophilic compound" refers to a compound that is characterized by its favourable interaction with lipids. Examples of such compounds include organic molecules which lack groups that may support a formal charge (e.g., carboxylic acid and amino groups) or which lack polar groups such as hydroxyl groups. Such compounds may be amino acid-based (e.g., amino acids, peptides, polypeptide and proteins), wherein the amino acids are exclusively or predominantly hydrophobic (e.g., leucine, valine, etc.). Examples of hydrophobic bioactive agents useful for various medical applications include propanidid, propofol, alphadione, lidocaine, lignocaine, echinomycin, miconazole nitrate, taxanes (also known as taxines or taxoids) such as paclitaxel and docetaxel, podophyllotoxins, camptothecins such as camptothecin, 9-aminocamptothecin, 9-nitrocamptothecin, camptothecin-11 ("Irinotecan"), topotecan, vinca alkaloids and their analogs (vincristine, vinorelbine, vindesine, vintripol, vinxaltine, ancitabine), lipophilic anthracyclines, decarbazine, lonidamine, piroxantrone, anthrapyrazoles, etoposide, bleomycin, 6-aminochrysene, navelbine, tributyrin, teniposide, platinum-based agents, praziquantel, cyclosporin A, 18-hydroxydeoxycorticosterone, rapamycin, prednisolone, vitamin A, vitamin E, purpurin, tin etiopurpurin, porphyrins, paraaminobenzoic acid, diazepam, delta 9-tetrahydrocannabinol, BBB-MDP, verapamil and nifedipine. In one embodiment, the bioactive agent is lidocaine or lignocaine.

In another embodiment, the first phase comprises a bioactive agent. In this case the preferred bioactive agent is a "hydrophilic compound" or "lipophobic compound". The term "hydrophilic compound" refers to a compound that is soluble in water. Examples of hydrophilic bioactive agents useful for various medical applications would be well known to those skilled in the art, for example, lignocaine HCl.

Accordingly, in one aspect, the method and miniemulsion described above may form a delivery system for a bioactive agent. Due to the size of the emulsified particles being 1 μm or smaller, the delivery system described herein can be administered by topical, enteral or parenteral routes. For example, the delivery system can be administered orally, nasally, intravenously, intramuscularly, subcutaneously, sublingually, intrathecally, intraperitoneally, intratumorally, topically, transdermally or intradermally. The route of administration can depend on a variety of factors, such as the environment and therapeutic goals. Further non-limiting pharmaceutically suitable materials that may be incorporated in pharmaceutical preparations/compositions disclosed herein include absorption enhancers, pH-adjusting agents and buffers, osmolarity adjusters, preservatives, stabilizers, antioxidants, surfactants, thickening agents, co-solvents, emollients, dispersing agents, flavouring agents, colouring agents and wetting agents and ligands/pilote/targeting molecules. The delivery system may be in the form of a liquid, a powder, an aerosol, a capsule, a tablet, a suppository, a cream, a gel and an ointment. Exemplary types of liquid include a lotion and a spray. In particular embodiments, the delivery system is formulated for administration as a spray or as an aerosol. Methods for preparing appropriate formulations are well known in the art (see, for example, Hendrickson, R. Ed. Remington: The Science and Practice of Pharmacy, 21st ed.; Lippincott Williams & Wilkins: Baltimore Md., 2005).

In one particular example, the miniemulsion may be formulated into a composition capable of reducing pain sensation or nociception, whether the pain incurred is a result of disease, inflammation, trauma or psychosomatic reaction. The composition will therefore be administered as an effective amount to a subject in need of pain relief. The phrase "in need of pain relief" as applied to a subject herein embraces a subject suffering mild to intense pain at the time of administration of the composition, as well as a subject that can reasonably be expected to have an imminent onset of mild to intense pain, eg., within about 1 to about 2 hours and especially within about 30 minutes, if no pain relief is administered.

The term "effective amount" refers to that amount which is sufficient to induce or maintain pain relief when administered to a subject; i.e., a pain relieving amount. What constitutes an effective pain-relieving amount, or dose, of the composition depends, among other factors, on the body weight of the subject and the intensity of the pain being treated.

An "effective pain relieving concentration" or "effective pain relieving plasma concentration" as used herein is intended to mean a plasma level in a subject which when tested in a standardised test involving the subject scoring the severity of pain, achieves a mean score indicating pain relief. In one such test as described herein below, patients score pain on a scale of from 10 (no reduction in severity of pain) to 0 (complete relief of pain) and a mean score equal to or greater than a given value is deemed to constitute effective pain-relief. A mean score of 5.0 or less and, more preferably, 2.0 or less in such a test, as exemplified herein, is deemed to constitute effective pain relief. The skilled artisan will appreciate, however, that other approaches can be used to assess the severity of pain and relief from such pain.

Thus, one aspect of the miniemulsion method described herein involves a therapeutic method for pain relief in which a miniemulsion comprising lidocaine is administered to a subject, in a formulation which provides detectable pain relief. By "detectable pain relief", it is meant that the formulation produces effective pain relief which is measurable by a standard method such as that described above. For example, a formulation, which achieves a mean score of 5.0 or less and, more preferably, 2.0 or less on a scale of from 0 to 10 in a testing system as described above, is deemed to provide detectable pain relief. The disclosure is not limited to use of any particular type of formulation, so long as it exhibits the pharmacokinetic profile defined herein. In one embodiment, the miniemulsion is formulated into an aerosol spray comprising lidocaine or lignocaine for use in pain relief.

The miniemulsion or delivery system described herein can be administered to any desired subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as foetuses, whether male or female, are intended to be covered.

The disclosure will now be further described by way of reference only to the following non-limiting examples. It should be understood, however, that the examples following are illustrative only, and should not be taken in any way as a restriction on the generality of the disclosure described above.

EXAMPLES

Example 1 Miniemulsion Preparation

Miniemulsions of 100 g were prepared with various concentrations of surfactant using the following process:

| | |
|---|---|
| Lecithin | 1.00-3.00% w/w |
| Tween 80 (Polysorbate 80) | 1.50-4.50% w/w |

| | |
|---|---|
| Soybean oil | 14.50% w/w |
| Water for Injection (WFI) | up to weight |

Preparation A:
1. Polysorbate 80 was added to 80% of the WFI required for preparation of the miniemulsion and stirred until dispersed.
2. Lecithin was then added into the aqueous solution of Tween 80 and dispersed by homogenization using a rotor homogeniser for 2 minutes or until dispersed.

Preparation B:
1. Soybean oil.

Mixing A & B:
Preparation B was added into Preparation A drop by drop (slowly) and with continuous homogenisation using a rotor homogeniser at a speed of 10,000 rpm. The remaining WFI was added to make up to weight. The resultant mixture was homogenised using a rotor homogeniser at a speed of 18,000 rpm for 10 minutes.

Example 2 Stability of Miniemulsions with Different Concentrations of Surfactant The miniemulsions prepared in Example 1 were scored on stability after one month using a number of parameters as shown in Table 1. As can be seen from Table 1, the total concentration of surfactant had no significant impact on the overall stability of the miniemulsion.

TABLE 1

| Parameters | Form. 1 | Form. 2 | Form. 3 | Form. 4 | Form. 5 | Form. 6 | Form. 7 | Form. 8 | Form. 9 |
|---|---|---|---|---|---|---|---|---|---|
| Lecithin | 2.00 | 2.00 | 2.00 | 3.00 | 3.00 | 3.00 | 1.00 | 1.00 | 1.00 |
| Tween 80 | 4.50 | 3.00 | 1.50 | 4.50 | 3.00 | 1.50 | 4.50 | 3.00 | 1.50 |
| % Ratio of Creamy layer/total height | 15.00 | 17.11 | 20.00 | 22.00 | 17.00 | 19.00 | 16.00 | 18.00 | 20.20 |
| Cracking | No | No | No | No | No | No | Visible | Visible | No |
| Relative density | 1.04 | 1.05 | 1.04 | 1.05 | 1.05 | 1.04 | 1.05 | 1.04 | 1.05 |
| Viscosity (mPa) | 2.51 | 2.28 | 2.01 | 2.85 | 2.48 | 2.27 | 2.19 | 1.98 | 1.85 |
| Mean particle size (µm) | | | | | | | | | |
| Upper layer | 0.72 | 0.64 | 0.66 | 0.90 | 0.69 | 0.68 | 0.66 | 0.79 | 0.64 |
| Lower layer | 0.53 | 0.61 | 0.56 | 0.50 | 0.55 | 0.47 | 0.50 | 0.53 | 0.56 |
| Total emulsion | 0.66 | 0.73 | 0.72 | 0.65 | 0.68 | 0.70 | 0.73 | 0.68 | 0.73 |

Example 3 Miniemulsion Prepared with and without Sonication

A 1 kg batch of miniemulsion was prepared according to Example 1 according to the following formulation except that the addition of Preparation B to Preparation A was aided by a peristaltic pump and not added dropwise:

| | |
|---|---|
| Lecithin | 1.00% w/w |
| Tween 80 (Polysorbate 80) | 1.00% w/w |
| Soybean oil | 14.50% w/w |
| Water for Injection (WFI) | up to weight |

The resultant miniemulsion was then subjected to magnetic stirring, homogenisation for 2, 4 or 10 minutes and sonication for 5 minutes, with samples taken at each stage for particle size analysis. Briefly, the emulsion was stirred using a magnetic stirrer for 10 minutes before a first sample was taken. The emulsion was then homogenised using a rotor homogeniser for 10 minutes, with samples taken at 2, 4 and 10 minutes. The emulsion was then further processed with sonication for 5 minutes and a final sample taken.

Particle size was analysed by Mastersizer 2000 from Malvern and the median diameter, where 50% of the distribution is above and 50% is below a diameter (d(0.5)), was determined. As shown in Table 2, a d(0.5) of 0.680 µm was achieved by stirring with a magnetic stirrer only. Further, there was no significant decrease in d(0.5) with homogenisation and/or sonication indicating that the present method can produce a miniemulsion using low-energy methods.

TABLE 2

| Batch | d (0.5) |
|---|---|
| 2% w/w emulsifier - stirred | 0.680 µm |
| 2% w/w emulsifier - homogenised 2 min | 0.623 µm |
| 2% w/w emulsifier - homogenised 4 min | 0.659 µm |
| 2% w/w emulsifier - homogenised 10 min | 0.715 µm |
| 2% w/w emulsifier - 5 min sonication | 0.651 µm |

Example 4 Formation and Evaluation of Multilayered Micelle Structures

It was hypothesised that the addition of the lipophilic surfactant to the dispersed hydrophilic surfactant created a multilayered micelle structure. A miniemulsion of 100 g was prepared containing fluorescence dyes as follows:

| | |
|---|---|
| Lecithin | 2.00% w/w |
| Tween 80 (Polysorbate 80) | 4.50% w/w |
| Soybean oil | 14.50% w/w |
| Rhodamine | 0.010% w/w |
| Fluorescein sodium | 0.010% w/w |
| Water for Injection (WFI) | up to weight |

Preparation A:
1. Fluorescein sodium (water soluble) was dissolved in 50 g of water.
2. Tween 80 was added into the 50 g of water containing fluorescein sodium on magnetic stirrer until dispersed.

3. Lecithin was added to the aqueous solution of Tween 80 and dispersed by homogenisation using a rotor homogeniser for 10 minutes or until dispersed.

Preparation B:
1. Rhodamine was dissolved in the soybean oil by sonication for 20 minutes in warm water (40° C.).
2. The oil was then filtered through a 0.2 μm filter to remove any undissolved Rhodamine particles.

Mixing A & B:
Preparation B was added into Preparation A drop by drop (slowly) with continuous stirring by a magnetic stirrer at medium speed (5). A sample was collected at this stage and imaged using fluorescence microscopy (FIG. 1).

The remaining water was added to make up to weight. The final mixture was stirred with magnetic stirrer for 10 minutes (maximum speed of 10). The homogenisation process was excluded and the preparation stirred at medium speed instead to achieve a larger particle size, which can be more easily observed by fluorescence microscope at 400× magnification.

Figure 2:
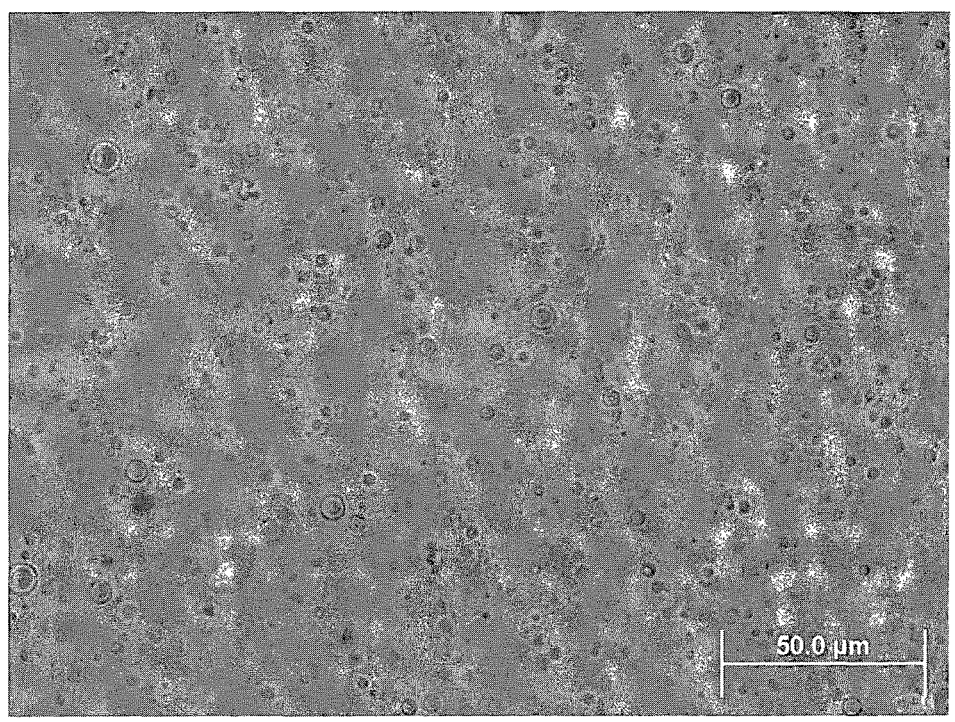
FIG. 2: Photograph of a miniemulsion by fluorescence microscope (400×).
Figure 3:
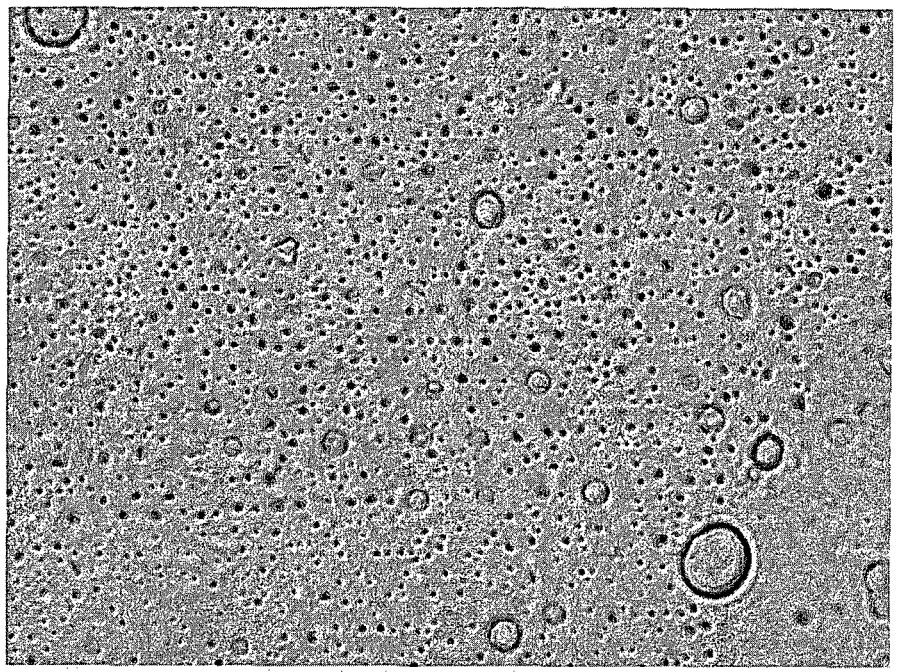
FIG. 3: Photograph of a miniemulsion by phase contrast light microscope (1000×).

A sample of the resultant preparation was then imaged using fluorescence microscopy (FIG. 2). As can be seen in FIGS. 1 and 2, the preparation comprises multilayered/spherical structures of lecithin and Tween 80 containing lipid within. A similar process was used to prepare a sample for light microscopy, except the fluorescein sodium was omitted from the aqueous phase (FIG. 3). It is thought that this multilayered structure increases the surface area of the interface and makes surfactant easily available at the interface during the emulsification process.

Further, the particles are spherical, which means that the particles are completely covered by surfactant molecules and there is minimum surface available for particle interaction compared with other forms of particles.

Lastly, this example demonstrates the ability for the miniemulsion to incorporate hydrophilic agents (fluorescin sodium) and lipophilic agents (rhodamine).

Example 5 Alternative Miniemulsion Preparations

The following variations on the formulations mentioned above were also prepared and are stable from 3 to 6 months.

| Lecithin | 2.00 g |
| Tween 80 (Polysorbate 80) | 2.50 g |
| Soybean oil | 25.00 g |
| Isopropyl alcohol | 10 ml |
| Water for Injection (WFI) | up to 100 g |

Preparation A:
1. Tween 80 was dissolved in 80% of the WFI by stirring.
2. 1.0 g of the lecithin was added into the aqueous solution of Tween 80 and dispersed by homogenization using a rotor homogeniser for 5 minutes.

Preparation B:
1. The remaining lecithin was added to the oil followed by the isopropyl alcohol and sonicated for 20 minutes at 40° C. to dissolve the lecithin and remove the solvent.

Mixing A & B:
Preparation B was added into Preparation A drop by drop (slowly) with continuous homogenisation using a rotor homogeniser at 10,000 rpm. The remaining WFI was then added to make up to weight.

| Glyceryl monostearate | 5.00 g |
| Tween 80 (Polysorbate 80) | 2.50 g |
| Soybean oil | 10.00 g |
| Water for Injection (WFI) | up to 100 g |

Preparation A:
1. Tween 80 was dissolved in 80% of the WFI by stirring.
2. The glyceryl monostearate was added into the aqueous solution of Tween 80 and mixed well.

Preparation B:
1. Soybean oil.

Mixing A & B:
Preparation B was added into Preparation A drop by drop (slowly) with continuous homogenisation using a rotor homogeniser at 10,000 rpm. The remaining WFI was added to make up to weight.

| Span 20 (Sorbitan monolaurate) | 2.00 g |
| Tween 80 (Polysorbate 80) | 2.50 g |
| Soybean oil | 25.00 g |
| Water for Injection (WFI) | up to 100 g |

Preparation A:
1. Tween 80 was dissolved in 80% of the WFI by stirring.
2. 1.0 g of the Span 20 was added into the aqueous solution of Tween 80 and dispersed by homogenization using a rotor homogeniser for 5 minutes.

Preparation B:
1. The remaining Span 20 was added to the oil and stirred for 20 minutes at 40° C. to dissolve Span 20.

Mixing A & B:
Preparation B was added into Preparation A drop by drop (slowly) with continuous homogenization using a rotor homogeniser at 10,000 rpm. The remaining WFI was added to make up to weight.

Example 6 Miniemulsion Preparation

A miniemulsion of 150 g was prepared containing lignocaine as follows:

| Phosphotidyl choline | 3.00 g | 2.00% w/w |
| Tween 80 (Polysorbate 80) | 6.75 g | 4.50% w/w |
| Soybean oil | 21.75 g | 14.50% w/w |
| Lignocaine | 4.50 g | 3.00% w/w |
| Water for Injection (WFI) | up to weight | |

Preparation A:
1. Tween 80 was added into 50 g of WFI and homogenized using a rotor homogeniser for 5 minutes at 10,000-15,000 rpm.
2. Phosphotidyl choline was added to the aqueous solution of Tween 80 and dispersed by homogeniser for 2 minutes or until dispersed.
3. The aqueous solution was sterilized in an autoclave at 121° C. for 15 minutes.

Preparation B:
1. The soybean oil was sterilised at 215° C. for 2 hours or by filtration through 0.2 μm filter.
2. Lignocaine was dissolved in the sterilised oil by sonication for 20 minutes in warm water (40° C.).

Mixing A & B:
Preparation B was added into Preparation A drop by drop (slowly) by passing through 0.2 μm sterile filter and with continuous homogenisation using a rotor homogeniser at 10,000 rpm. The remaining WFI was added to make up to weight. The final mixture was homogenized using a rotor homogeniser at 18,000 rpm for 10 minutes.

Example 7 Stability at Room Temperature and at 4° C.—Lignocaine Concentration

To ensure that the lignocaine was not degraded over time, two separate batches ("Batch 1" and "Batch 2") of the emulsion formed according to the method in Example 6 were tested for lignocaine stability when stored at room temperature and at 4° C. (ie. with and without refrigeration) over a period of 322 days. Stability was tested by measuring the concentration of lignocaine in the preparation at a particular time point by HPLC and comparing this to the actual quantity added during the formation of the preparation. Briefly, lignocaine was extracted from samples of the preparations by liquid-liquid extraction at each time point. The method was optimised by using different solvent systems and was also validated as per Pharmacopoeia guidelines.

Step 1: 0.5 g emulsion was weighed in 25 mL volumetric flask. The emulsion sample was dissolved in isopropyl alcohol before being made up to volume with additional isopropyl alcohol (Solution A). 2 mL aliquots of Solution A were then transferred to screw capped test tubes followed by addition 4 mL of dichloromethane. The mixture was gently shaken for 4-5 times by inversion.

Step 2: 4 mL of 0.1M HCl was added to the solvent mixture. Lignocaine was extracted in 0.1M HCl by gentle shaking for 5 mins followed by 5 mins centrifugation at 1000 rpm. The aqueous upper layer was removed and collected in 20 mL volumetric flask (Solution N1). Step 2 was repeated twice more for a total of three times.

Step 3: Solution A/1 was made up to volume by 0.1M HCl. A small amount of the sample was filtered through 0.5 µm filter and injected for HPLC analysis. The HPLC conditions were as follows:

| 1. Mobile Phase: | |
|---|---|
| 25 mM Phosphoric Acid (2.883 g): | 60%: 600 mL |
| Methanol | 40%: 400 mL |
| Total Volume | 1000%: 1 L |
| 2. Flow rate: | 1 mL/min |
| 3. Wavelength: | 210 nm |
| 4. Column (Alltech): | Apollo C18, 5 µm, Length: 50 mm ID: 4.6 mm |
| 5. Integration Parameters: | Area of rejection: 10000 Threshold: 3 Peak width: 0.05 |

Figure 4:
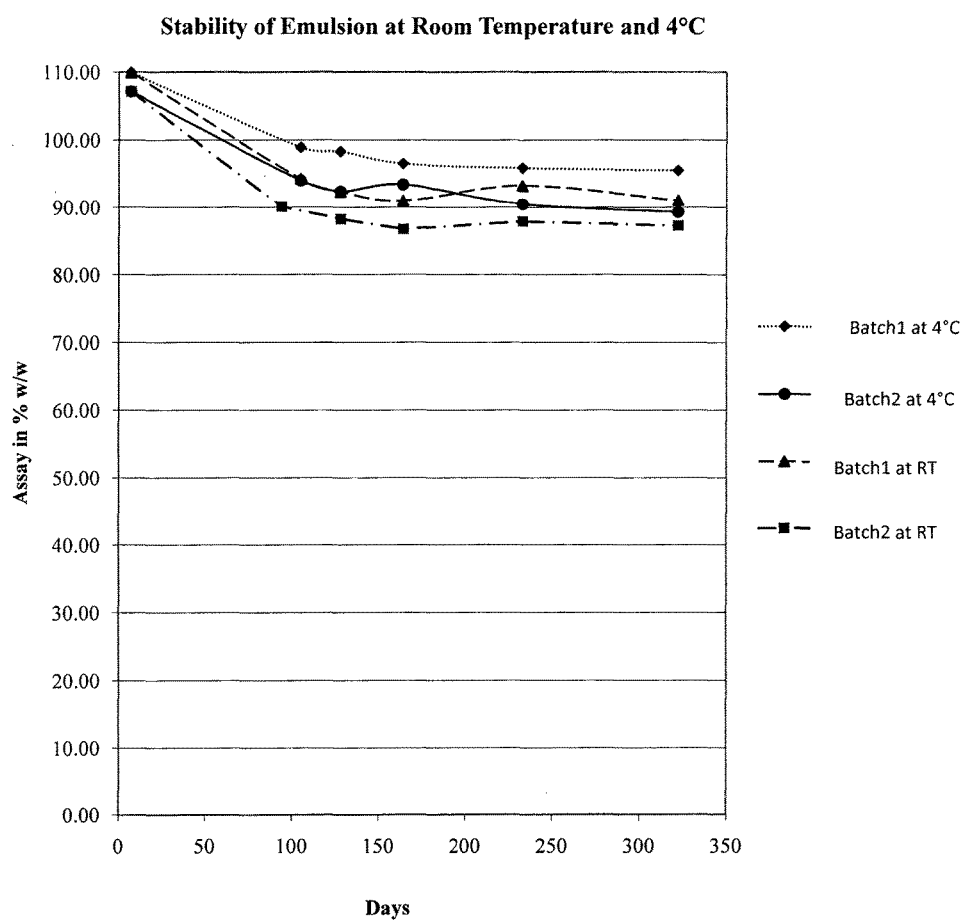
FIG. 4: Stability of lignocaine in a miniemulsion stored at room temperature and 4° C. over 322 days.

The concentration of lignocaine in the sample was compared to the original concentration of lignocaine in the preparation and was expressed as a percentage. As shown in FIG. 4, the degradation of lignocaine was occurring at approximately the same rate in the preparations stored at room temperature and the preparations stored at 4° C. Accordingly, this result indicates that the miniemulsion prepared by the method describes has a long shelf-life as it is stable and preserves the concentration of agents when stored at room temperature over an extended period of time.

Example 8 Stability at Room Temperature and at 4° C.—Particle Size

Batches 1 and 2, prepared as described in Examples 6 and 7, were also tested for stability when stored at room temperature and at 4° C. (ie. with and without refrigeration) over a period of 236 days by measuring particle size. Particle size was analysed by Mastersizer 2000 from Malvern and the median diameter, where 50% of the distribution is above and 50% is below a diameter (d(0.5)) and where 90% of the distribution is below a diameter (d(0.9)), was determined. As shown below in Tables 3 and 4, there was almost no difference observed between mean distribution d(0.5) and d(0.9) in the preparations stored at room temperature and the preparations stored at 4° C.

TABLE 3

| | Batch 1 | | | |
|---|---|---|---|---|
| | At Room Temperature | | At 4° C. | |
| Days | d (0.5) | d (0.9) | d (0.5) | d (0.9) |
| 19 | 0.699 | 1.309 | 0.699 | 1.309 |
| 145 | 0.2 | 0.369 | 0.242 | 0.458 |
| 236 | 1.191 | 2.869 | 1.186 | 2.955 |

TABLE 4

| | Batch 2 | | | |
|---|---|---|---|---|
| | At Room Temperature | | At 4° C. | |
| Days | d (0.5) | d (0.9) | d (0.5) | d (0.9) |
| 19 | 0.2 | 0.3 | 0.2 | 0.3 |
| 145 | 0.2 | 0.369 | 0.22 | 0.404 |
| 236 | 1.168 | 2.752 | 1.164 | 2.739 |

Example 9 Characterisation of Miniemulsion: Particle Size Report

Figure 6:
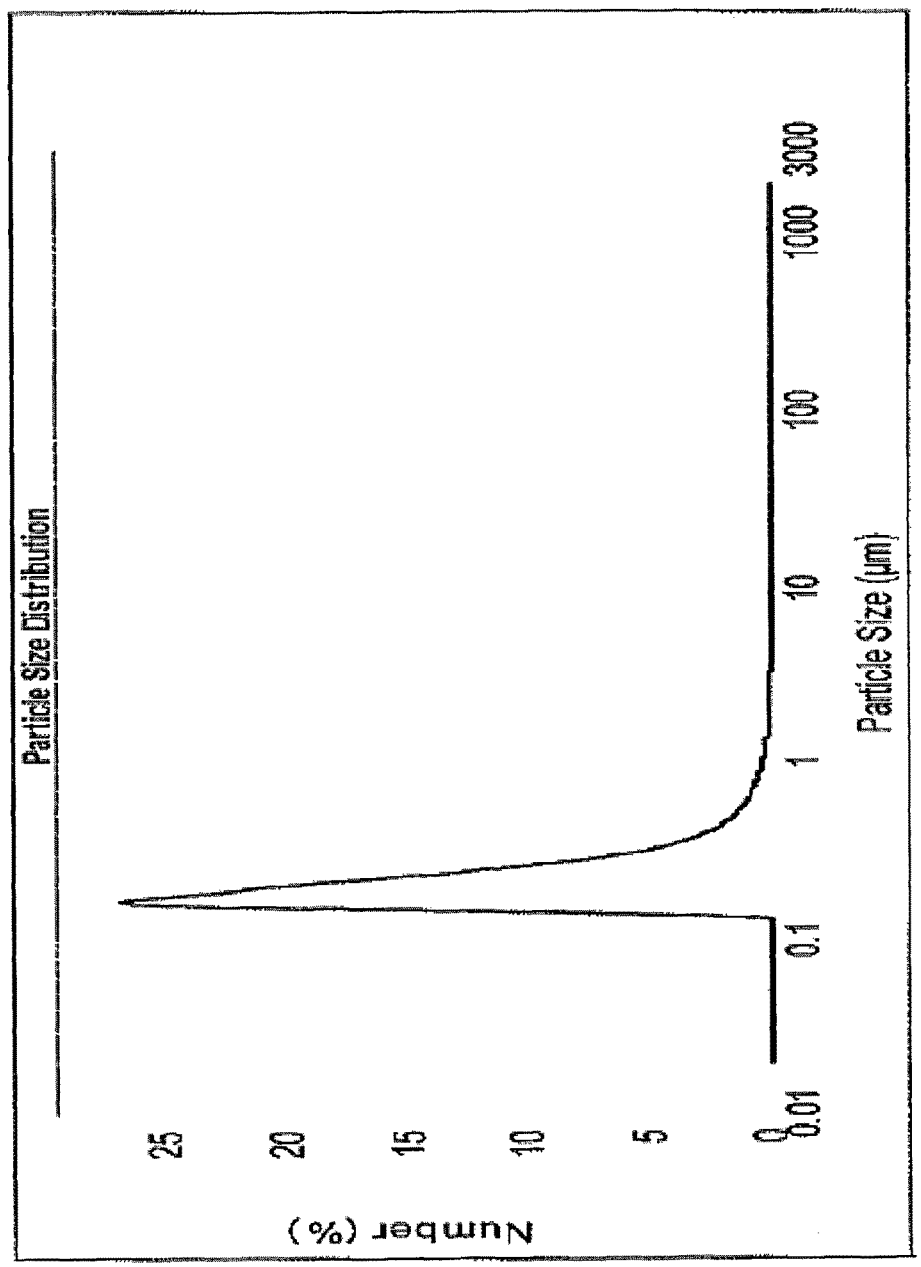
FIG. 6: Particle size distribution graph for a miniemulsion prepared in a batch size of 150 g.
Figure 7:
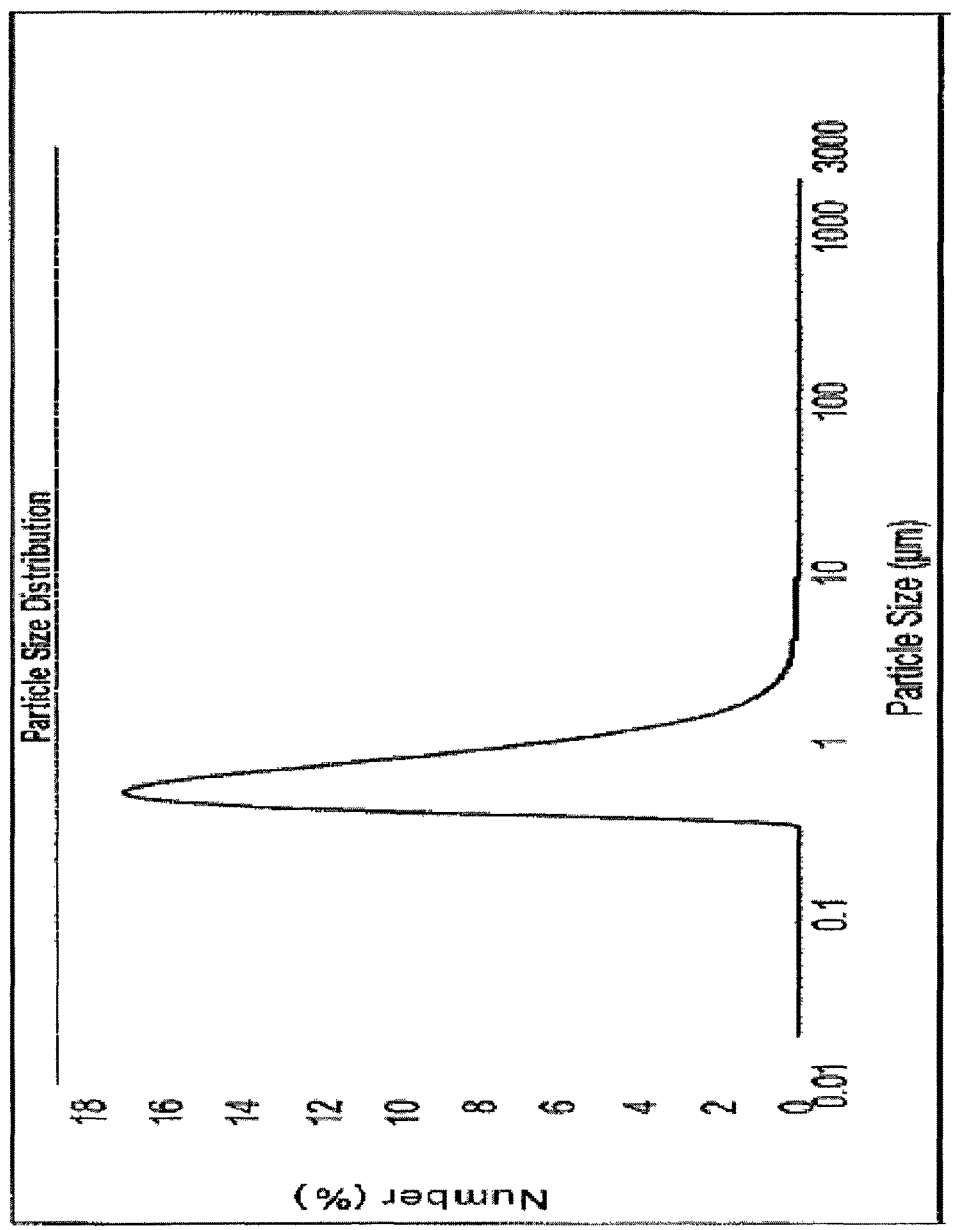
FIG. 7: Particle size distribution graph for a miniemulsion prepared in a batch size of 1 kg.

A sample of the miniemulsion prepared by the method described in Example 6 was analysed by Mastersizer 2000 from Malvern. A scaled up batch of 1 kg was also prepared using the method in Example 6 (except the addition of Preparation B to Preparation A was aided by a peristaltic pump and not added dropwise) and analysed. Briefly, 2-3 drops emulsion was added drop wise in 100 mL of deionised water. The results of the test are shown in FIGS. 5-7. Almost 100% (99.24%) of the particles analysed from the 150 g batch had a size of less than 1 µm or less. This was slightly higher than in the 1 kg batch (85.00%). Further, approximately 50% of the particles in the 150 g batch were between 200 nm and 1 µm and approximately 85% of the particles in the 1 kg batch were between 200 nm and 1 µm.

The particles in the 150 kg batch were on average slightly smaller (d(0.5)=0.202 µm) than those in the 1 kg batch (d(0.5)=0.619 µm), which is thought to be due to a technical sampling issue. Nonetheless, these results indicate that the miniemulsion could be successfully scaled-up to a commercial batch size without significantly effecting particle size.

Example 10 Stability of Miniemulsion Prepared in a Batch Size of 1 kg

The stability of the 1 kg batch was also tested to ensure the emulsion would remain stable in its scaled-up form. Several parameters of stability were examined and the results are shown in Table 5.

Particle size was analysed by Mastersizer 2000 from Malvern and the median diameter, where 50% of the distribution is above and 50% is below a diameter (d(0.5)), was determined. The concentration of lignocaine (% w/w) and % assay of lignocaine were determined using the HPLC method described in Example 7.

The peroxide value was determined using the standardised method A from the British Pharmacopoeia Volume IV, Appendix XF 2010; London: Her Majesty's Stationery Office for the Department of Health. Briefly, 2.50 g of the emulsion was placed in a 250 ml conical flask fitted with a ground-glass stopper. 30 ml of a mixture of 2 volumes of chloroform R and 3 volumes of glacial acetic acid was added and the flask shaken until the emulsion dissolves. 0.5 ml of saturated potassium iodide solution R was then added and the flask shaken again for exactly 1 min before 30 ml of water was added. 0.01 M sodium thiosulphate was titrated into the solution slowly with continuous vigorous shaking until the yellow colour was almost discharged. 5 ml of starch solution was then added and the titration continued, shaking vigorously, until the colour was discharged (n1 ml of 0.01 M sodium thiosulphate). A blank test was then carried out under the same conditions (n2 ml of 0.01 M sodium thiosulphate). The volume of 0.01 M sodium thiosulphate used in the blank titration must not exceed 0.1 ml.
Calculation:

$$Ip = \frac{10(n_1 - n_2)}{m}$$

The pH of the emulsion was measured by a digital pH meter. The pH meter was calibrated using a standard buffer solution (pH 4 and 7) before measuring emulsion samples. The pH was also tested using Duo test pH meter.

TABLE 5

| Test | Time | | | | | | |
|---|---|---|---|---|---|---|---|
| | 3 Months | 6 Months | 9 Months | 14 Months | 15 Months | 18 Months | 30 Months |
| Concentration of Lignocaine (% w/w) | 2.99 | 2.89 | 2.77 | 2.85 | 2.99 | — | — |
| % Assay of Lignocaine | 99.74 | 96.39 | 92.24 | 94.94 | 99.7 | — | — |
| Mean Particle Size (0.5) | 0.619 | 0.616 | 0.650 | 0.669 | 0.669 | 0.635 | 0.668 |
| pH of Emulsion | 8.4 | 8.65 | 8 | 7.75 | 7.75 | 7.45 | 7.10 |
| Peroxide Value of Emulsion (mEq/kg) | — | 3 | 2 | 1.55 | 4 | 1.5 | 1.89 |

As can be seen from Table 5, none of the parameters changed significantly over the 15 month period, indicating that the emulsion, even when scaled-up to 1 kg, is stable for over 2 years.

Figure 8B:
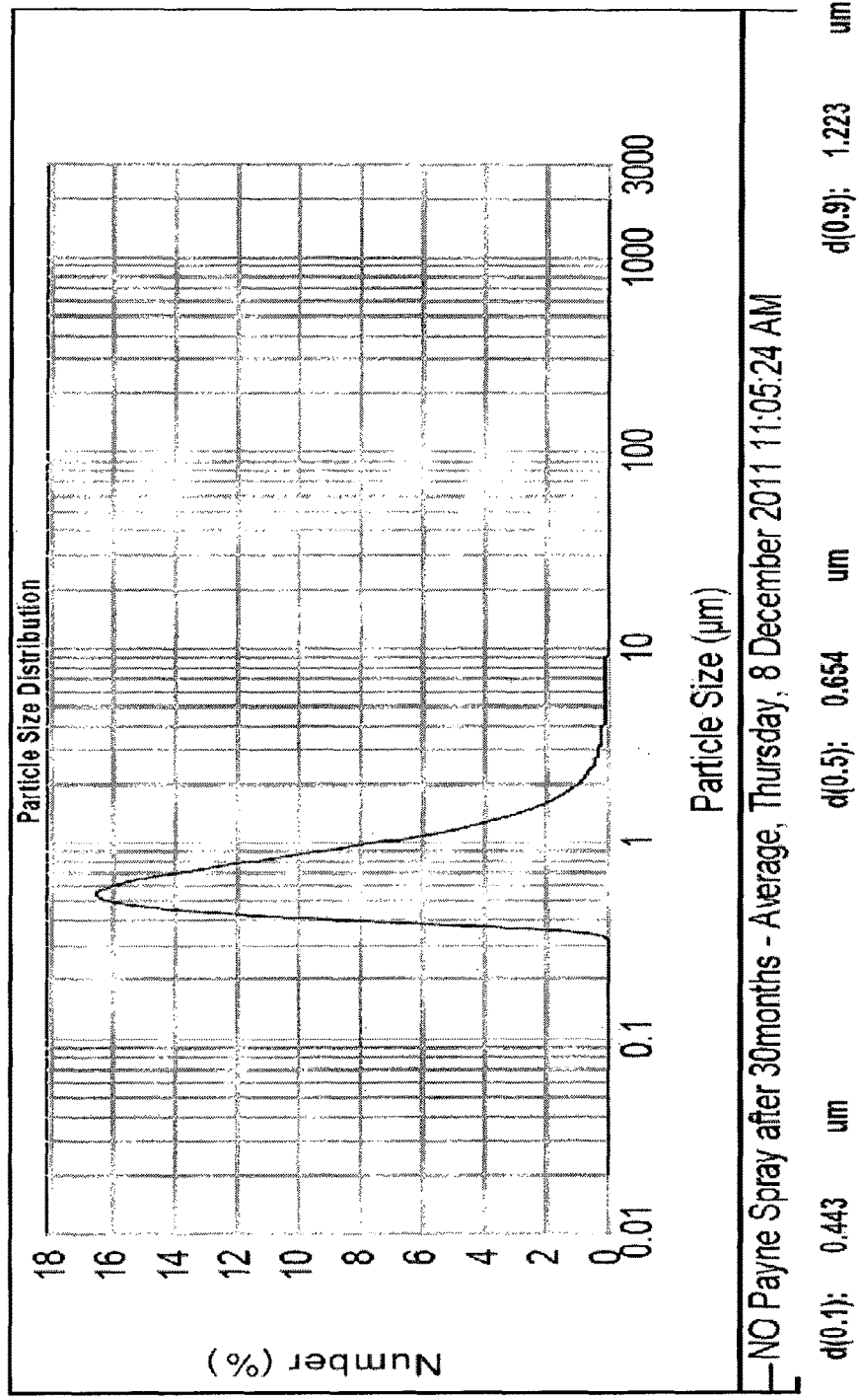
FIG. 8: Particle size distribution for a miniemulsion prepared in a batch size of 1 kg and stored at room temperature for 30 months.

Importantly, the mean particle size does not increase over time. An increase in particle size is a key indicator of emulsion instability. However, even after 30 months (914 days) at room temperature, the increase in particle size is negligible (FIG. 8). Accordingly, these results show that the emulsion is stable for more than 2 years and 6 months at room temperature.

Oxidation of oil is another key indicator of emulsion instability. As shown above, the peroxide value does not vary greatly over time, indicating that the oil is not oxidizing in the emulsion. The small variation in peroxide seen is due to the nature of analysis. Further, all values are in agreement with the Pharmacopeia standard for Injectable products.

Example 11 Miniemulsion Preparation Comprising 40% w/w Lipid

A miniemulsion of 100 g was prepared containing lignocaine HCl, salicylic acid and eucalyptus oil as follows:

| Phosphotidyl choline | 1.00 g | 2.00% w/w |
|---|---|---|
| Tween 80 (Polysorbate 80) | 2.00 g | 4.00% w/w |
| Coconut oil | 10.00 g | 20.00% w/w |
| Salicylic acid | 1.00 g | 2.00% w/w |
| Lignocaine HCL | 0.50 g | 1.00% w/w |
| Benzoic Acid | 0.05 g | 0.10% w/w |
| Isopropyl alcohol | 2.00 g | 4.00% w/w |
| Liquid Paraffin | 10.00 g | 20.00% w/w |
| Water for Injection (WFI) | up to weight | |

Preparation A:
1. Lignocaine HCl and benzoic acid were dissolved in 20 g of water.
2. Tween 80 was added into 20 g of WFI containing lignocaine HCl and benzoic acid and homogenized using a rotor homogeniser for 5 minutes at 10,000-15,000 rpm.
3. Phosphotidyl choline was added to the aqueous solution of Tween 80 and dispersed by homogenized using a rotor homogeniser for 20 minutes or until dispersed.

Preparation B:
1. Coconut oil was melted at 40° C. and mixed with liquid paraffin with gentle stirring.
2. Salicylic acid was dissolved in the oil by sonication with 2 mL of isopropyl alcohol for 20 minutes in warm water (40° C.).

Mixing A & B:
Preparation B was added into Preparation A drop by drop (slowly) with continuous homogenisation using a rotor homogeniser at 10,000 rpm. The remaining WFI was added to make up to weight. The final mixture was homogenized at 18,000 rpm for 10 minutes (most of the isopropyl alcohol is assumed to be evaporated during this process).

Figure 9B:
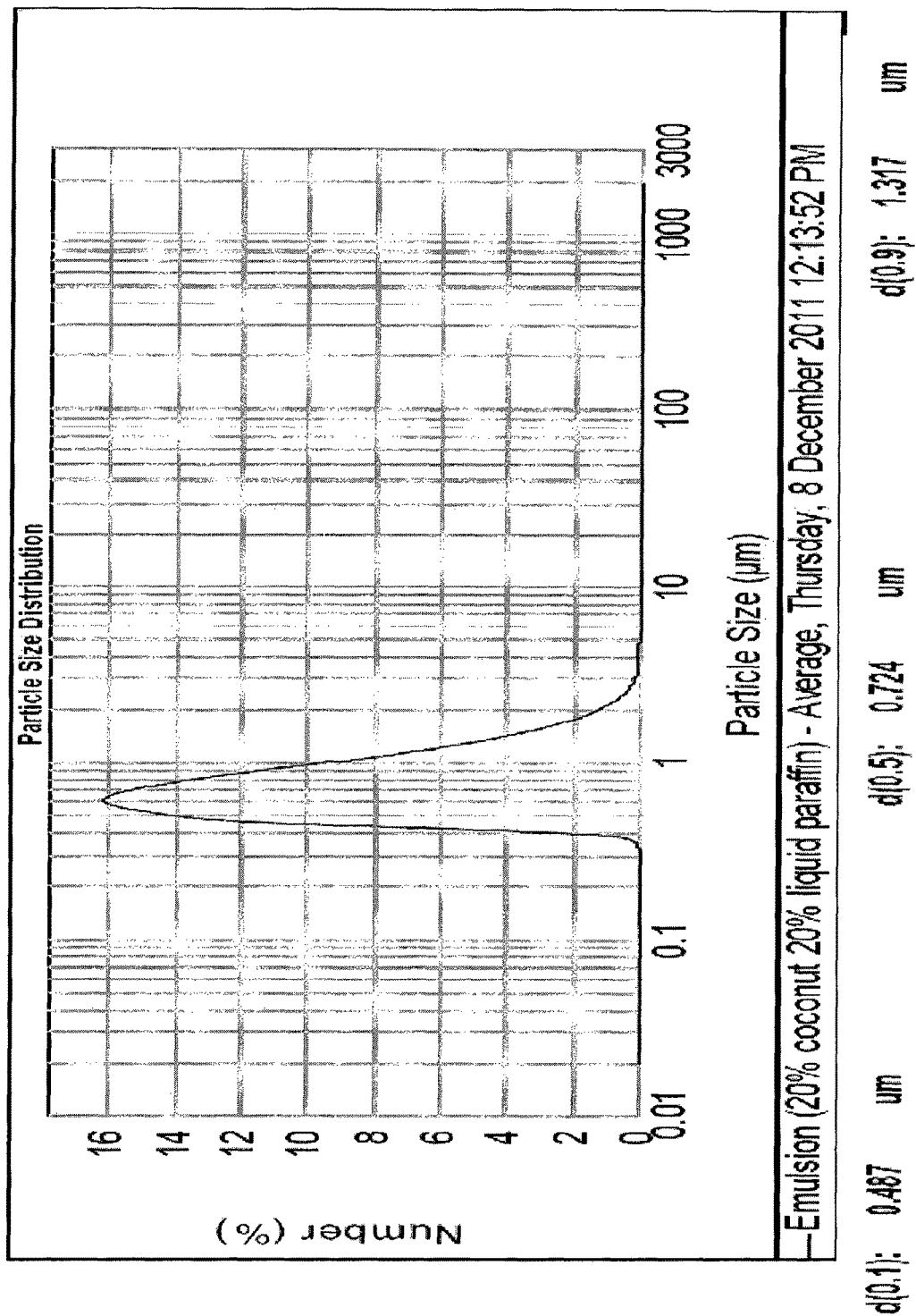
FIG. 9: Particle size distribution for a miniemulsion prepared containing 40% w/w lipid.

A sample of the miniemulsion was analysed by Mastersizer 2000 from Malvern. Briefly, 2-3 drops of emulsion were added drop wise in 100 mL of deionised water. The results of the test are shown in FIG. 9.

This example also demonstrates the ability for the miniemulsion to incorporate hydrophilic agents (lignocaine HCL) and lipophilic agents (salicylic acid).

Example 12 Use of the Miniemulsion to Treat Pain

The scaled-up 1 kg batch described above in Examples 9 and 10 was used to treat pain in patients receiving skin donor site dressing changes. The emulsion was delivered as a spray ("NS Spray") and tested against a traditional pain spray containing 4% xylocaine ("Xylocaine Spray").

Patients were randomly allocated to receive treatment with either the Xylocaine spray or NS Spray. One hour after the procedure patients gave a final pain score and rated their overall satisfaction. The patients scored pain on a scale of from 10 (no reduction in severity of pain) to 0 (complete relief of pain) and a mean score equal to or greater than a given value is deemed to constitute effective pain-relief. A mean score of 5.0 or less and, more preferably, 2.0 or less in the test was deemed to constitute effective pain relief.

Example 13 Pain Score Analysis

Figure 10:
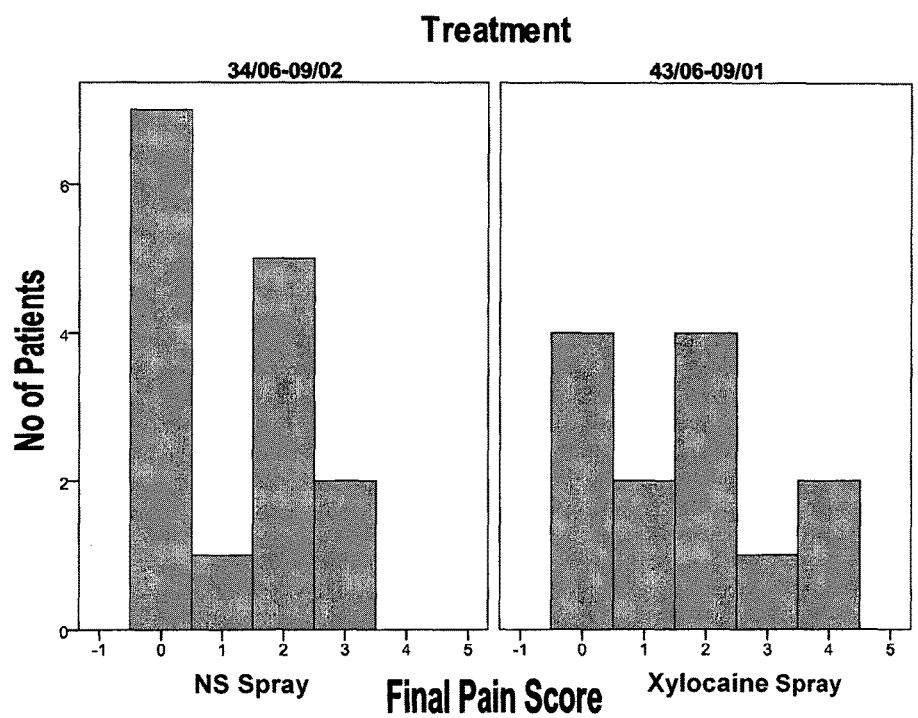
FIG. 10: Distribution of final pain scores from patients receiving NS Spray and Xylocaine Spray.

All patients recorded a pain score of less than 5 for their Final pain score (FIG. 10). As can be seen from FIG. 10, the NS Spray treatment was slightly more effective at reducing pain compared with the Xylocaine Spray.

Figure 11:
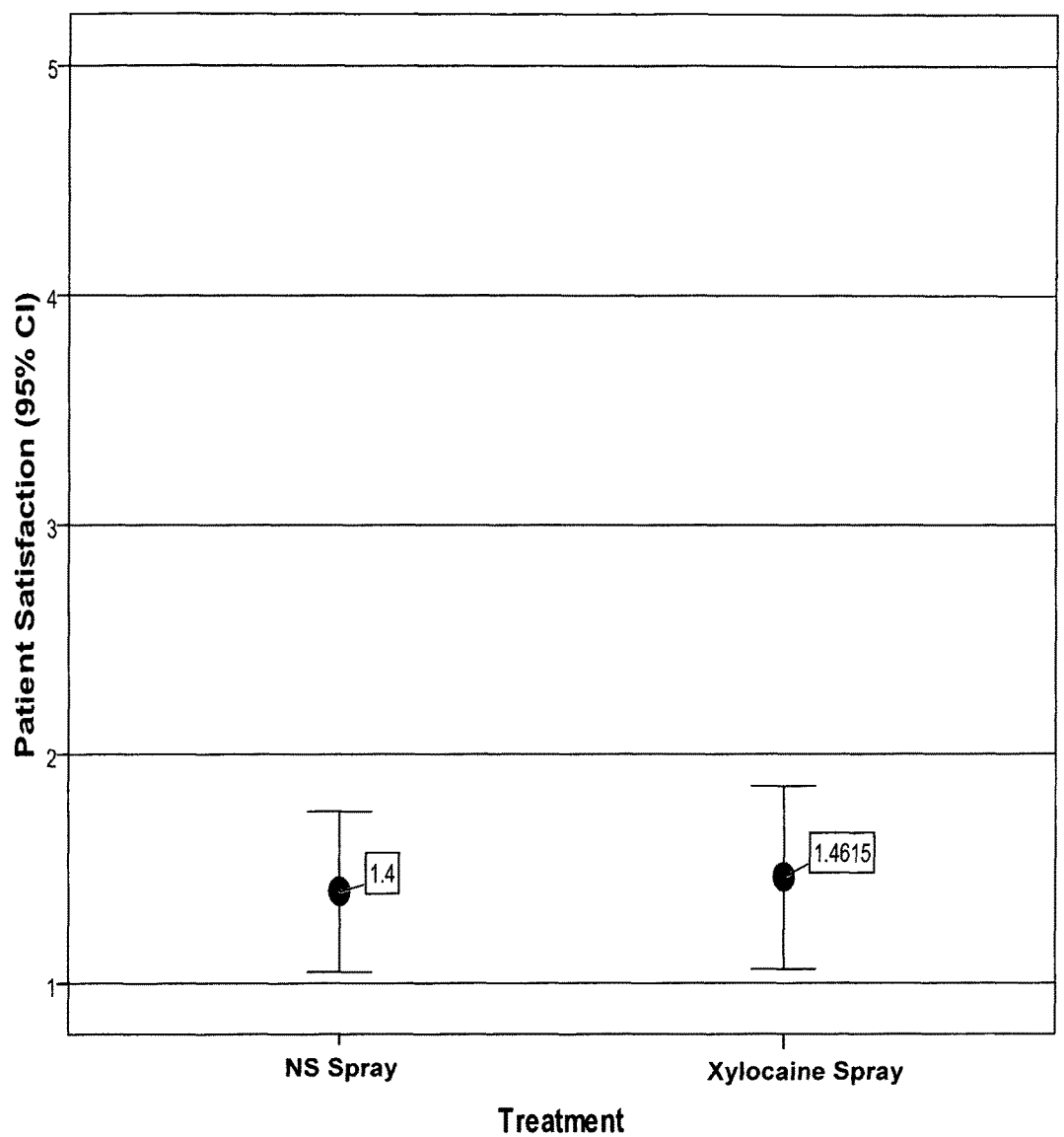
FIG. 11: Average patient satisfaction scores from patients receiving NS Spray and Xylocaine Spray (95% CI; 1=very satisfied and 5=very unsatisfied).

Patients were also asked on a scale of 1 to 5 how satisfied they were with the treatment (where 1 is very satisfied and 5 is very unsatisfied). Patients treated with the NS Spray gave an average satisfaction score of 1.4 (FIG. 11). Accordingly, patients were very satisfied with the NS Spray treatment and the NS Spray managed pain at least as well as the standard treatment and possibly had a longer lasting effect.

The invention claimed is:

1. A method for forming a delivery system for a lipophilic bioactive agent comprising the following sequential steps;
   a. preparing a first phase by:
      (i) dissolving polysorbate 80 in water above critical micelle concentration (CMC) to produce an aqueous phase; and then
      (ii) dispersing phosphatidylcholine in said aqueous phase to produce said first phase which first phase contains micelles of polysorbate 80 and phosphatidylcholine and comprises a multi-lamellar structure;
   b. preparing a second phase comprising soybean oil and a lipophilic bioactive agent; and
   c. adding the second phase to the first phase drop-wise or as a continuous flow or continuous stream during continuous mixing at a speed of between about 5,000 rpm and about 20,000 rpm, at a temperature of 40° C. or less and at an atmospheric pressure of less than 1,000 kPa to form a miniemulsion comprising between about 0.5% w/w and about 5% w/w polysorbate 80, between about 1% w/w and about 5% w/w phosphatidylcholine, between about 0.5% w/w and about 25% w/w soybean oil, and between about 0.2% w/w and about 5% w/w lipophilic bioactive agent; and
   wherein said delivery system comprises emulsified particles having a mean diameter of between 250 nm and 1 μm which are stable for 3 months or more between 2° C. and 30° C.

2. The method of claim 1, wherein said emulsified particles are stable for at least 2 years.

3. The method of claim 1, wherein said emulsified particles are stable for up to 3 years.

4. The method of claim 1, wherein the temperature used in step c is about 25° C. and about normal atmospheric pressure at sea level.

5. The method of claim 1, wherein the lipophilic bioactive agent is a lipophilic analgesic agent.

6. The method of claim 5, wherein the lipophilic analgesic agent is lidocaine.

7. A method for forming a delivery system for a lipophilic bioactive agent comprising the following sequential steps;
   a. preparing a first phase by:
      (i) dissolving a hydrophilic surfactant in water above critical micelle concentration (CMC) to produce an aqueous phase; and then
      (ii) dispersing lipophilic surfactant in said aqueous phase to produce said first phase which first phase contains micelles of hydrophilic surfactant and lipophilic surfactant and comprises a multi-lamellar structure;
   b. preparing a second phase comprising soybean oil and a lipophilic bioactive agent; and
   c. adding the second phase to the first phase drop-wise or as a continuous flow or continuous stream during continuous mixing at a speed of between about 5,000 rpm and about 20,000 rpm, at a temperature of 40° C. or less and at an atmospheric pressure of less than 1,000 kPa to form a miniemulsion comprising between about 0.5% w/w and about 5% w/w hydrophilic surfactant, between about 1% w/w and about 5% w/w lipophilic surfactant, between about 0.5% w/w and about 25% w/w soybean oil, and between about 0.2% w/w and about 5% w/w lipophilic bioactive agent; and
   wherein said delivery system comprises emulsified particles having a mean diameter of between 250 nm and 1 μm which are stable for 3 months or more between 2° C. and 30° C.

8. The method of claim 7, wherein said emulsified particles are stable for at least 2 years.

9. The method of claim 7, wherein said emulsified particles are stable for up to 3 years.

10. The method of claim 7, wherein the temperature used in step c is about 25° C. and about normal atmospheric pressure at sea level.

11. The method of claim 7, wherein the lipophilic bioactive agent is a lipophilic analgesic agent.

12. The method of claim 7, wherein the lipophilic analgesic agent is lidocaine.

* * * * *